(12) United States Patent
Trost et al.

(10) Patent No.: US 6,919,456 B2
(45) Date of Patent: Jul. 19, 2005

(54) CATALYTIC COMPOSITIONS AND METHODS FOR ASYMMETRIC ALDOL REACTIONS

(75) Inventors: Barry M. Trost, Los Altos, CA (US); Hisanaka Ito, Tokyo (JP)

(73) Assignee: The Board of Trustees of the Leland Stanford Junior University, Standford, CA (US)

( * ) Notice: Subject to any disclaimer, the term of this patent is extended or adjusted under 35 U.S.C. 154(b) by 65 days.

(21) Appl. No.: 10/452,082

(22) Filed: May 30, 2003

(65) Prior Publication Data

US 2004/0019239 A1 Jan. 29, 2004

Related U.S. Application Data

(62) Division of application No. 09/999,802, filed on Oct. 31, 2001, now Pat. No. 6,610,889.
(60) Provisional application No. 60/244,833, filed on Nov. 1, 2000.

(51) Int. Cl.[7] .................. C07D 211/36; C07D 405/00; C07D 207/40
(52) U.S. Cl. .................. 546/186; 546/208; 540/596; 540/597; 540/602; 548/523; 548/518
(58) Field of Search .................. 540/596, 597, 540/602; 546/186, 208; 548/523, 518

(56) References Cited

PUBLICATIONS

Trost, J Am Chem Soc, 2000, vol 122, pp 12003–12004.*
Trost, J Am Chem Soc, 2001, vol 123, pp 3367–3368.*

* cited by examiner

*Primary Examiner*—D. Margaret Seaman
(74) *Attorney, Agent, or Firm*—LeeAnn Gorthey; Perkins Coie LLP

(57) ABSTRACT

Methods and compositions are provided for the direct catalytic asymmetric aldol reaction of aldehydes with donor molecules selected from ketones and nitroalkyl compounds. The reactions employ as catalyst a Group 2A or Group 2B metal complex of a ligand of formula I, as defined further herein.

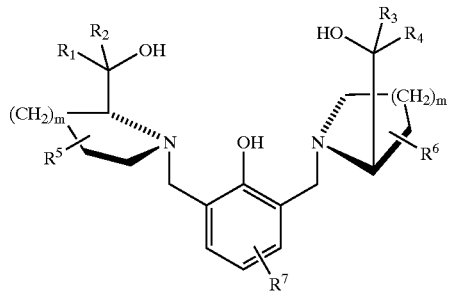

I

8 Claims, 3 Drawing Sheets

US 6,919,456 B2

CATALYTIC COMPOSITIONS AND METHODS FOR ASYMMETRIC ALDOL REACTIONS

This application is a divisional application of U.S. application Ser. No. 09/999,802, filed Oct. 31, 2001, now U.S. Pat. No. 6,610,889, which in turn claims priority to U.S. provisional application Ser. No. 60/244,833, filed Nov. 1, 2000. Both of these applications are hereby incorporated by reference in their entirety.

This invention was made with the support of the National Science Foundation and the National Institutes of Health, General Medical Sciences. Accordingly, the U.S. Government may have certain rights in this invention.

FIELD OF THE INVENTION

The present invention relates to methods and compositions for the direct catalytic asymmetric aldol reaction of aldehydes with ketones or nitroalkyl compounds.

REFERENCES

Agami, C., Platzer, N., Sevestre, H. *Bull. Soc. Chim. Fr.* 358 (1987).

Arnaud, N., Picard, C., Cazaux, L., Tisnès, P. *Tetrahedron* 53:13757 (1997).

Bach, T. *Angew. Chem., In. Ed. Engl.* 33:417 (1994).

Carreira, E. M., in *Comprehensive Asymmetric Catalysis*, Jacobsen, E. N., Pfaltz, A., Yamamoto, H., Eds. (Springer, Heidelberg, 1999), vol. 3, 998.

Crisp, G. T. and Turner, P. D., *Tetrahedron* 56:407–15 (2000).

Gröger, H., Vogl, E. M., Shibasaki, M. *Chem. Eur. J.* 4:1137 (1998).

Heathcock, C. H., in *Asymmetric Synthesis*, J. D. Morrison, Ed. (Academic Press, New York, 1984), vol. 3, part B, p. 111.

Hoffmann, T. et al., *J. Am. Chem. Soc.* 120:2768 (1998).

Johnson, J. S., Evans, D. A. *Acc. Chem. Res.* 33:325 (2000).

Kim, B. M., Williams, S. F., Masamune, S., in *Comprehensive Organic Synthesis*, Trost, B. M., Fleming, I., Eds (Pergamon Press, Oxford, 1991), vol. 2, chap. 1.7, pp. 239.

Knudsen, K. R. et al., *J. Am. Chem. Soc.* 123:5843 (2001).

List, B., Lerner, R. A., Barbas, C. F., III *J. Am. Chem. Soc.* 122:2395 (2000).

Luzzio, F. A., *Tetrahedron* 57:915 (2001).

Machajewski, T. D., Wong, C.—H. *Angew. Chem. Int. Ed.* 39:1352 (2000).

Mahrwald, R. *Chem. Rev.* 99:1095 (1999).

Matt, C. et al., *J. Org. Chem.* 62:234 (1997)

Mukaiyama, T. *Org. React.* 28:203 (1982).

Nakayawa, M., Nakao, H., Watanabe, K. *Chem. Lett.* 391 (1985).

Nelson, S. G. *Tetrahedron: Asymmetry* 9:357 (1998).

Notz, W., List, B. *J. Am. Chem. Soc.* 122:7386 (2000).

Noyori, R. et al *Angew. Chem., Int. Ed. Engl.* 30:49 (1991).

Paterson, I. et al., *Tetrahedron Lett.* 30:997 (1989).

Ramachandran, P. V. et al., *Tetrahedron Lett.* 37:4911 (1996).

Sasai, H. et al., *J. Am. Chem. Soc.* 114:4419 (1992).

Seebach, D. et al., *Liebigs Ann. Chem.* 1215–1232 (1989).

Seyden-Penne, J. *Chiral Auxiliaries and Ligands in Asymmetric Synthesis* (Wiley, New York, 1995), Ch. 6, pp. 306–361.

Shibasaki, M. et al., *Angew. Chem. Intl. Ed. Engl.* 36:1236 (1997).

Shibasaki, M., Sasai, H. *Top. Stereochem.* 22:201 (1999).

Soai, K. et al., *Chem. Rev.* 92:833 (1992).

Takayama, S., McGarvey, G. J., Wong, C. H. *Chem. Soc. Rev.* 26:407 (1997).

Trost, B. M., *Angew. Chem. Int. Ed. Engl.* 34:259 (1995).

Van der Boom, M. E. et al., *J. Am. Chem. Soc.* 120:6531 (1998).

Yazawa, K. et al., JP Kokai No. 10-327890 (1998).

Yoshikawa, N. et al., *J. Am. Chem. Soc.* 121:4168 (1999).

BACKGROUND OF THE INVENTION

Few chemical reactions have reached the prominence of aldol-type reactions in the synthesis of complex molecules (Mukaiyama, 1982; Kim et al., 1991; Heathcock, 1984). The classical aldol reaction is highly atom economic (Trost, 1995) but suffers from poor chemo- and regioselectivity. In current practice, aldol reactions typically employ a preformed enolate, enol, or equivalent; an example is the Mukaiyama reaction, which employs an enol silyl ether. These reactions generally provide greater selectivity, but require stoichiometric amounts of base and/or adjunct reagents (e.g. silylating agents), thus decreasing the atom efficiency of the process.

Most asymmetric versions of the aldol reaction reported to date rely upon the use of chiral auxiliaries (Seyden-Penne, 1995). Mukaiyama-type processes using asymmetric catalysts have also been reported (Johnson et al., 2000; Carreira, 1998; Mahrwald, 1999; Gröger et al., 1998; Nelson, 1998; Bach, 1994); as noted above, these require prior stoichiometric formation of the nucleophile. Methods for direct catalytic asymmetric aldol addition, without prior stoichiometric formation of the nucleophile, are thus being sought. Processes employing both biological-type (e.g. catalytic antibodies) (Machajewski et al., 2000; Takayama et al., 1997; Hoffmann et al., 1998) and non-biological-type (Yoshikawa et al., 1999; Shibasaki et al., 1999; List et al., 2000; Notz et al., 2000; Agami et al., 1987; Nakayawa et al., 1985) catalysis have been reported. In all of these cases, however, significant excesses of the donor and/or large amounts of catalyst must be employed, and unbranched aldehyde substrates remain problematic.

The Henry (nitro-aldol) reaction (see e.g. Luzzio et al.) is also a fundamental C—C bond forming reaction which generates stereogenic centers. There are very few examples to date of catalytic asymmetric nitroaldol reactions. Shibasaki et al. have carried out such reactions using chiral heterobimetallic (rare earth-alkali metal) catalysts, and Jorgensen et al. have reported the catalytic asymmetric aza-Henry reaction of silyl nitronates with imines. However, the use of silyl nitronates as nucleophiles undermines the atom economy of the reaction.

SUMMARY OF THE INVENTION

The present invention includes, in one aspect, a method of conducting an enantioselective aldol reaction between an aldehyde and a donor molecule selected from a nitroalkyl compound and a ketone bearing an α-hydrogen, the method comprising:

contacting the aldehyde and donor compound in the presence of a catalytic amount of an asymmetric catalyst, wherein the catalyst is a complex of a Group 2A or Group 2B metal with a chiral ligand of formula I:

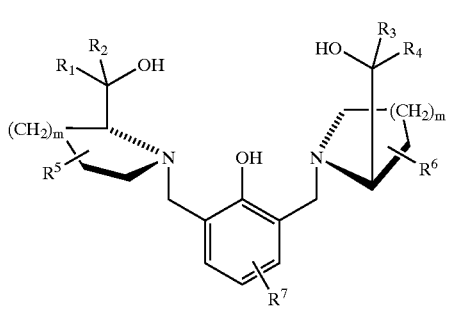

where $R^1$–$R^4$ are aryl groups, which may be the same or different, each of which is unsubstituted or substituted with one or more substituents X, where each X is independently selected from alkyl, alkenyl, alkynyl, aryl, aralkyl, aralkenyl, aralkynyl, alkoxy, aryloxy, amide, alkyl- or aryl sulfonyl, sulfonamide, hydroxy, cyano, nitro, and halogen, and wherein $R^1$ and $R^2$, or $R^3$ and $R^4$, or both of these combinations, may be linked at an α-carbon of each the group to form a tricyclic or larger ring system;

m is an integer from 0 to 3, is preferably 1 or 3, and is more preferably 1;

each of $R^5$ and $R^6$ represents one or more substituents independently selected from the group consisting of hydrogen and X as defined above; and $R^7$ represents one or more substituents on the phenyl ring independently selected from the group consisting of hydrogen, X as defined above, and a further fused ring;

under conditions effective to produce an aldol reaction product which is enriched in one of the possible stereoisomeric products of such reaction.

In selected embodiments, the Group 2A or Group 2B metal is Zn, Cd, Mg, Ca, or Ba. Preferably, the metal is zinc.

In additional embodiments, each of $R^1$–$R^4$ is phenyl or naphthyl (α or β), unsubstituted or substituted with a group selected from X as defined above. In preferred embodiments, each of $R^1$–$R^4$ is phenyl or naphthyl (α or β), unsubstituted or substituted with lower alkyl, lower alkoxy, or halogen. In additional preferred embodiments, each of $R^5$ and $R^6$ is hydrogen.

In further embodiments, each substituent $R^7$ is selected from the group consisting of hydrogen, lower alkyl, lower alkenyl, aryl, aralkyl, aryloxy, lower alkoxy, and halogen.

In carrying out the reaction, the donor compound and aldehyde are typically present in a molar ratio between about 1:1 and 10:1. The amount of catalytic complex is preferably about 2.5 to 10 mole percent relative to moles of aldehyde. When the donor compound is an α-hydroxyketone, the molar ratio is preferably between about 1:1 and 1.5:1, and the amount of catalytic complex is preferably about 2.5 to 5 mole percent. When the donor compound is a nitroalkyl compound, the molar ratio is preferably about 5:1 to 10:1.

In another aspect, the invention provides a catalytic composition consisting of a complex of a Group 2A or Group 2B metal with a chiral ligand of formula I, as defined above. The Group 2A or Group 2B metal is preferably selected from Zn, Cd, Mg, Ca, and Ba, and is most preferably zinc. Selected embodiments of the chiral ligand are described above. Exemplary chiral ligands include ligands 1a–1n, and preferably ligands 1a, 1c–d, and 1m, as disclosed herein.

The invention also encompasses a catalytic composition formed by contacting, in a suitable solvent, a chiral ligand of formula I, as defined above, with a Group 2A or Group 2B metal compound which is capable of generating a metal alkoxide upon reaction with an alcohol. The compound may be, for example, a dialkyl metal, dialkoxy metal, alkyl metal halide, alkyl (dialkylamino) metal, or alkyl (diarylamino) metal. The metal is preferably selected from Zn, Cd, Mg, Ca, and Ba, and is most preferably zinc. In selected embodiments, the metal compound is a di(lower alkyl) zinc compound. Selected embodiments of the chiral ligand are described above.

In addition, the invention provides a chiral ligand of formula I:

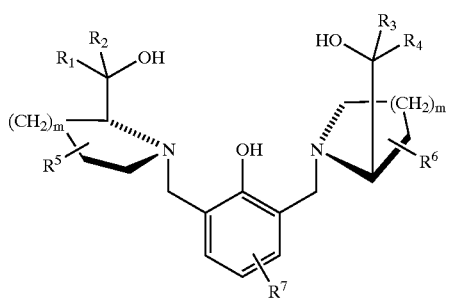

where $R^1$–$R^4$ are aryl groups, which may be the same or different, each of which is unsubstituted or substituted with one or more substituents X, where each X is independently selected from alkyl, alkenyl, alkynyl, aryl, aralkyl, aralkenyl, aralkynyl, alkoxy, aryloxy, amide, alkyl- or aryl sulfonyl, sulfonamide, hydroxy, cyano, nitro, and halogen, wherein $R^1$ and $R^2$, or $R^3$ and $R^4$, or both of these combinations, may be linked at an α-carbon of each the group to form a tricyclic or larger ring system;

m is an integer from 0 to 3;

each of $R^5$ and $R^6$ represents one or more substituents independently selected from the group consisting of hydrogen and X as defined above; and $R^7$ represents one or more substituents on the phenyl ring independently selected from the group consisting of hydrogen, X as defined above, and a further fused ring.

In groups $R^1$ to $R^4$, the substituents defined as group X are preferably selected from alkyl, alkenyl, aryl, aralkyl, alkoxy, aryloxy, ester, amide, sulfonamide, alkyl- or arylsulfonyl, nitro, and halogen; more preferably selected from alkyl, alkenyl, alkoxy, nitro, and halogen; and most preferably selected from lower alkyl, lower alkoxy, and halogen. In one embodiment, each of groups $R^1$–$R^4$ is phenyl, unsubstituted or substituted with a group selected from X above, preferably selected from lower alkyl, lower alkoxy, and halogen. In specific embodiments, $R^1$–$R^4$ are identical and each is unsubstituted phenyl, α- or β-naphthyl, or p-methoxyphenyl.

The value of m is preferably 1 or 3, and most preferably 1. $R^5$ and $R^6$ are preferably selected from hydrogen, lower alkyl, lower alkenyl, lower alkynyl, and aryl. Each group $R^5$ and $R^6$ is preferably hydrogen. In another preferred embodiment, the nitrogen heterocycles are substituted such that chiral centers are not formed; i.e. by having two identical substituents at a given position, as in a gem-dimethyl group.

The substituents defined as group X for $R_7$ are preferably selected from alkyl, alkenyl, aryl, aralkyl, alkoxy, aryloxy, ester, amide, sulfonamide, alkyl- or arylsulfonyl, nitro, and halogen; and more preferably selected from alkyl, alkenyl, alkoxy, aryl, aralkyl, aryloxy, and halogen.

Representative ligands include compounds 1a–1n, shown in FIGS. 1–12. In selected embodiments, the chiral ligand is selected from the group consisting of ligands 1a, 1c–d, and 1m.

These and other objects and features of the invention will become more fully apparent when the following detailed description of the invention is read in conjunction with the accompanying drawings.

DETAILED DESCRIPTION OF THE INVENTION

I. Definitions

Figure 1:
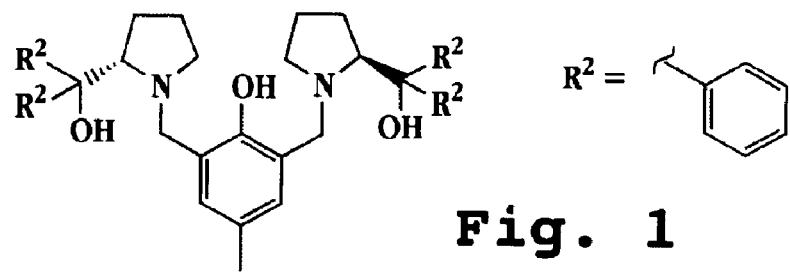
FIGS. 1–12 show representative chiral ligands (1a–1n) of the invention.

The terms below have the following meanings unless indicated otherwise.

The "chiral ligand of formula I" also encompasses ligands having the opposite absolute configuration to that depicted (i.e. mirror image compounds).

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples of cycloalkyl groups are cyclopropyl, methyl cyclopropyl, cyclobutyl, cyclopentyl, ethylcyclopentyl, and cyclohexyl.

"Alkenyl" refers to an acyclic monovalent radical containing carbon and hydrogen, which may be branched or a straight chain, and which contains at least one carbon-carbon double bond. The alkenyl group may be monounsaturated or polyunsaturated. Similarly, "alkynyl" refers to such a radical having at least one carbon-carbon triple bond.

"Lower" alkyl (alkenyl, alkynyl, alkoxy, etc.) refers to a group having 1 to 6 carbons, preferably 1 to 4 carbons.

"Aryl" refers to a substituted or unsubstituted monovalent aromatic radical having a single ring (e.g., benzene) or two or three condensed rings (e.g., naphthyl; phenanthryl). Groups having a single ring (monocyclic) or two condensed rings (bicyclic) are generally preferred, with monocyclic groups being particularly preferred. The term includes heteroaryl groups, which are aromatic ring groups having one or more nitrogen, oxygen, or sulfur atoms in the ring, such as furyl, pyrrole, pyridyl, and indole. Carbocyclic aryl groups are preferred for the chiral ligands of the invention. By "substituted" is meant that one or more ring hydrogens in the aryl group is replaced, independently, with halogen, alkyl, alkoxy, nitro, cyano, amide, tertiary amino, alkyl- or aryl sulfonyl, sulfonamide, hydroxy, or halo(lower alkyl).

"Aralkyl" refers to an alkyl, preferably lower alkyl, substituent which is further substituted with an aryl group; one example is a benzyl group. Similarly, "aralkenyl" and "aralkynyl" refer to alkenyl or alkynyl substituents further substituted with an aryl group.

"Nitroalkyl compound" refers to a compound which contains a nitromethyl (—$CH_2NO_2$) or nitromethylene (>$CHNO_2$) moiety and is able to form a stable carbanion on abstraction of an α-hydrogen (on the carbon adjacent the nitro group), the simplest example being nitromethane ($CH_3NO_2$).

II. Catalytic Compositions

In one aspect, the invention provides catalytic compositions which are effective to catalyze an aldol reaction between an aldehyde and a donor molecule bearing an acidic α-hydrogen, e.g. a ketone or a nitroalkyl compound, to produce an aldol reaction product which is enriched in one of the possible stereoisomeric products of such a reaction. In particular, the reaction is highly enantioselective.

A. Structure

The catalytic composition of the invention is a complex of a Group 2A or Group 2B metal with a chiral ligand of formula I.

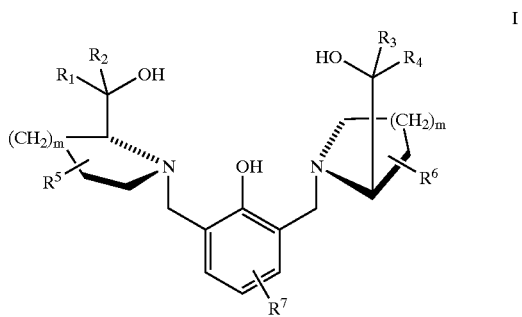

I

The Group 2A or Group 2B metal is preferably selected from the group consisting of Zn, Cd, Mg, Ca, and Ba, is more preferably Zn or Mg, and is most preferably Zn. In a series of aldol reactions conducted as described herein, employing magnesium and zinc complexes, zinc complexes generally gave the higher enantioselectivities.

For ease of synthesis, the ligand preferably has C2 symmetry; however, this is not required.

In formula I, $R^1$–$R^4$ are aryl groups, which may be the same or different. Each of these groups is optionally substituted with one or more substituents X, where each X is independently selected from alkyl, alkenyl, alkynyl, aryl, aralkyl, aralkenyl, aralkynyl, alkoxy, aryloxy, amide, sulfonamide, alkyl- or arylsulfonyl, hydroxy, cyano, nitro, and halogen. In addition, any two adjacent groups (i.e. $R^1$ and $R^2$, $R^3$ and $R^4$, or both combinations) maybe linked via an α-carbon of each the group (i.e. a ring carbon adjacent the carbon atom linked to the carbinol carbon) to form a tricyclic or larger ring system; e.g., a fluorene, xanthene, or dihydroanthracene ring system.

In groups $R^1$ to $R^4$, the substituents defined as group X are preferably selected from alkyl, alkenyl, aryl, aralkyl, alkoxy, aryloxy, ester, amide, sulfonamide, alkyl- or arylsulfonyl, nitro, and halogen; more preferably selected from alkyl, alkenyl, alkoxy, nitro, and halogen; and most preferably selected from lower alkyl, lower alkoxy, and halogen. In one embodiment, each of groups $R^1$–$R^4$ is phenyl, unsubstituted or substituted with a group selected from lower alkyl, lower alkoxy, and halogen. In specific embodiments, $R^1$–$R^4$ are identical and each is unsubstituted phenyl, α- or β-naphthyl, o-tolyl, biphenyl, or p-methoxyphenyl.

The value of m is from 0 to 3, inclusive; m is preferably 1 or 3, and is most preferably 1. $R^5$ and $R^6$ represent one or more substituents on the respective N-heterocycles, independently selected from hydrogen, lower alkyl, lower alkenyl, lower alkynyl, and aryl. To avoid the presence of additional chiral centers on the nitrogen heterocycles, each group $R^5$ and $R^6$ is preferably hydrogen. However, the nitrogen heterocycles could be substituted such that chiral centers are not formed; i.e. by having two identical substituents at a given position, as in a gem-dimethyl group.

Although not depicted in formula I, the nitrogen heterocycle may contain a further heteroatom, as in a morpholino ring.

In selected embodiments, each of $R^5$ and $R^6$ is selected from hydrogen, lower alkyl, lower alkenyl, lower alkoxy, and halogen. Preferably, $R^5$ and $R^6$ are both hydrogen or both represent a gem-dimethyl group; most preferably, $R^5$ and $R^6$ are both hydrogen.

$R^7$ represents one or more groups on the phenyl ring independently selected from the group consisting of hydrogen, X as defined above, and a further fused ring, e.g. to form a naphthyl group. The substituents defined as group X for $R_7$ are preferably selected from alkyl, alkenyl, aryl, aralkyl, alkoxy, aryloxy, ester, amide, sulfonamide, alkyl- or arylsulfonyl, nitro, and halogen; and more preferably selected from alkyl, alkenyl, alkoxy, aryl, aralkyl, aryloxy, and halogen. Multiple groups $R^7$ can be present and can be the same or different.

Figure 2:
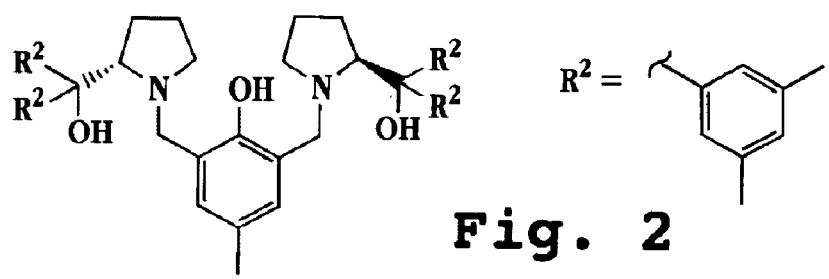
Figure 3:
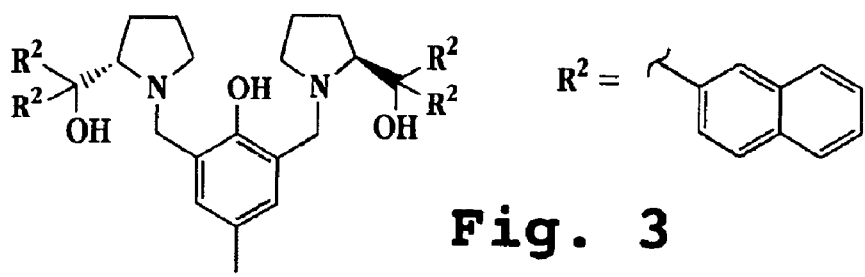
Figure 4:
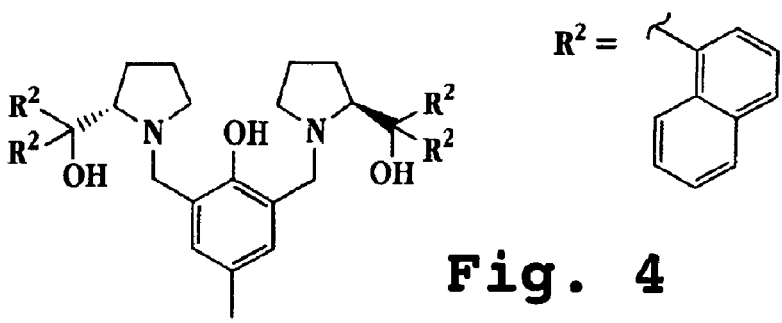
Figure 5:
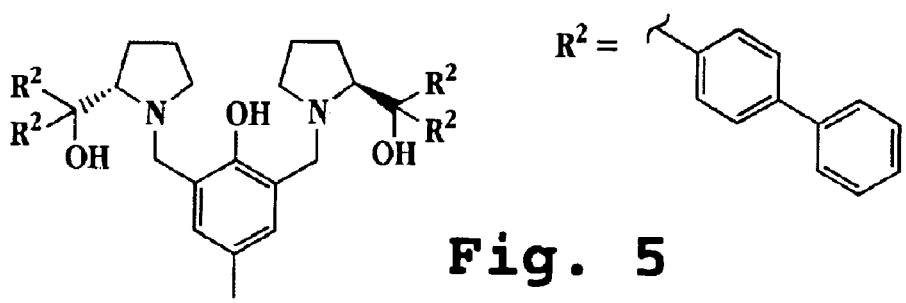
Figure 6:
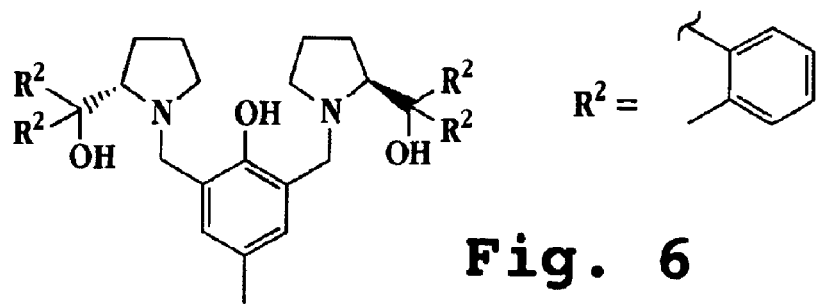
Figure 7:
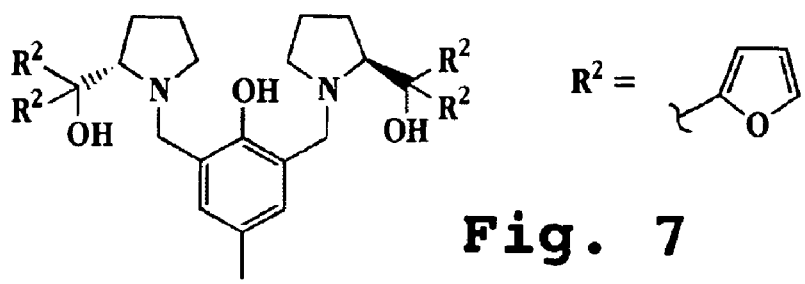
Figure 8:
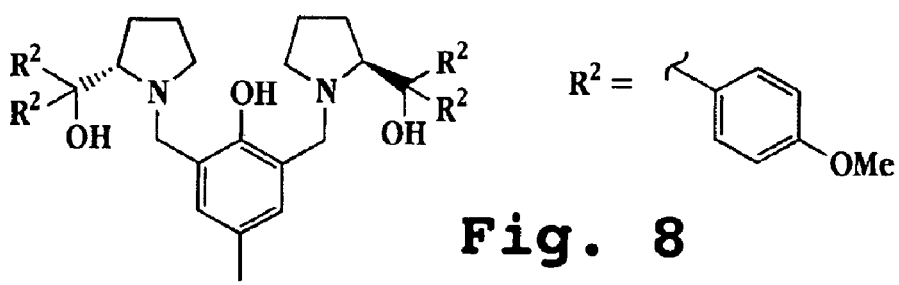
Figure 9:
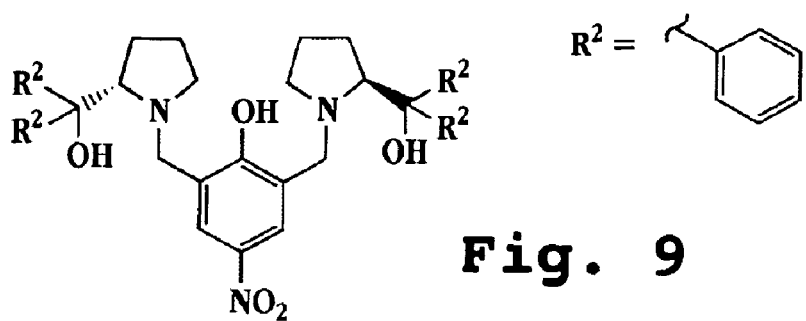
Figure 10:
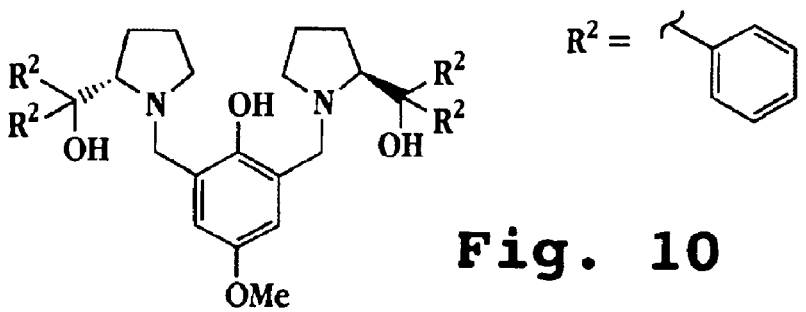
Figure 11:
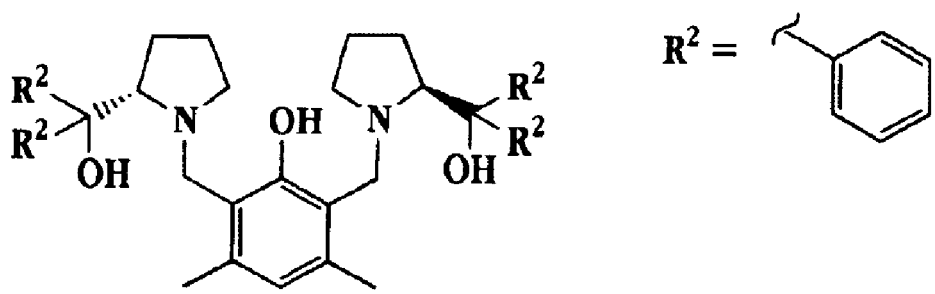
Figure 12:
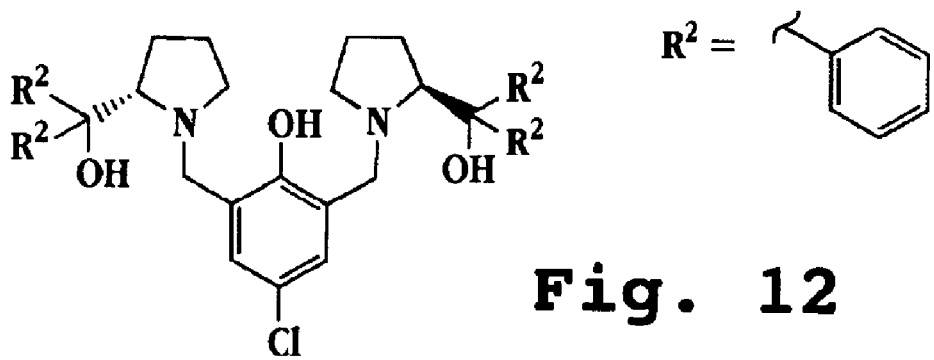

Representative ligands include compounds 1a–1n, as shown in FIGS. 1–12.

The stoichiometry of metal to ligand in the catalytic complex was examined via the evolution of ethane gas upon reaction of ligand 1a with $Et_2Zn$. Addition of two equivalents of $Et_2Zn$ per ligand 1 liberated three equivalents of ethane. Addition of water to this complex liberated the fourth equivalent of ethane. This observation supports a 2:1 stoichiometry of metal ion to ligand in the complex. In addition, exposure of the complex to acetic acid in the inlet of an electrospray mass spectrometer produced a series of peaks consistent with the formula $C_{45}H_{47}N_2O_5Zn_2$, i.e. a bimetallic zinc complex of 1a having bound acetate.

B. Preparation

B1. Ligand Synthesis

The availability of a variety of enantiomerically pure a-amino acids provides a convenient route to the chiral α-amino alcohol moiety of the ligands. For example, an ester of L-proline (natural S configuration) or D-proline (R configuration) was used to prepare ligands 1a–1n, as described in Examples 1–13 below. The R- and S-isomers of other 2-carboxyl N-heterocycles, such as 2-azetidine carboxylic acid, 2-piperidine carboxylic acid, and 1H-hexahydroazepine-2-carboxylic acid, are commercially available, and syntheses permitting preparation of substituted derivatives have been reported (e.g. Seebach et al., 1989; Yazawa et al., 1998).

A convenient synthesis of ligands of formula I starts with 2,6-hydroxymethylation of a phenol, as described, for example, in Van der Boom et al., 1998 and Arnaud et al., 1997 (reaction of p-cresol). Reaction of other para-substituted phenols is described in Examples 10 and 11, below. Para-substituted phenols are preferred for this reaction (addition of formaldehyde) to preclude reaction at the para-position. Differently substituted 2,6-hydroxymethylated phenols can be prepared by methods known in the art. As shown in Examples 12A–B, for example, 3,5-dimethyl-2,6-bis(hydroxymethyl)phenol (for ligand 1m) was prepared via the reaction of dimethyl acetonedicarboxylate with 2,4-pentanedione. Crisp et al., 2000, describes the preparation of 2,6-bis(hydroxymethyl) phenol in high yield by $LiAlH_4$ reduction of dimethyl (2-hydroxy isophthalate).

The primary hydroxyl groups of the 2,6-bis (hydroxymethyl)phenol compound are converted to efficient leaving groups, e.g. bromide or tosylate. The resulting compound is then reacted with two equivalents of a chiral 2-carboxy N-heterocycle. Addition of an aryl carbon nucleophile, such as an aryl Grignard reagent, is then employed to convert each carboxyl group (preferably in ester form) to the tertiary alcohols bearing groups $R^1$ to $R^4$. This general route was used to prepare ligands 1a–1c, 1g–h, and 1k, as described in Examples 1, 3–4, 8–9 and 11, below.

Alternatively, N-Boc protected R- or S-proline, or another of the 2-carboxyl N-heterocycles noted above, is first reacted with an aryl carbon nucleophile, such as an aryl Grignard. The tertiary alcohol product is deprotected and reacted with a 2,6-bis(bromomethyl)phenol compound. Examples of this route, used to prepare ligands 1a, 1d–f, 1j, and 1n, are described in Examples 2, 5–7, 10 and 13. The intermediate diphenylprolinol is commercially available. The route described in Examples 5–7 may be used to prepare other diarylprolinols.

During synthesis of variously substituted ligands, protecting groups, as known in the art, may be used as necessary for any reactive substituents that may be present.

The following table gives the structures of ligands 1a–1n, where, in structure 1, m is 1 and $R^5$ and $R^6$ are hydrogen.

| Designation | $R^7$ | $R^1$–$R^4$ |
| --- | --- | --- |
| 1a | 4-methyl | phenyl |
| 1b | 4-methyl | 3,5-xylyl |
| 1c | 4-methyl | 2-naphthyl |
| 1d | 4-methyl | 1-naphthyl |
| 1e | 4-methyl | biphenyl |
| 1f | 4-methyl | o-tolyl |
| 1g | 4-methyl | furyl |
| 1h | 4-methyl | 4-methoxyphenyl |
| 1j | 4-nitro | phenyl |
| 1k | 4-methoxy | phenyl |
| 1m | 3,5-dimethyl | phenyl |
| 1n | 4-chloro | phenyl |

B2. Generation of Catalyst

The catalytic composition is formed by contacting a chiral ligand of formula I with a Group 2A or 2B metal compound which is capable of generating a metal alkoxide upon reaction with an alcohol, and specifically upon reaction with the hydroxyl groups of the ligands of formula I. Such compounds include dialkyl metals $R_2M$, alkyl (or alkenyl) metal halides RMX, metal alkoxides $M(OR)_2$, alkyl (dialkylamino) metal compounds $RMNR_2$, and alkyl (diarylamino) metals (where the groups R may vary and are preferably lower alkyl or lower alkenyl). As noted above, preferred metals include Zn, Cd, Mg, Ca, and Ba. In one embodiment, the compound is diethyl zinc; diphenylamino ethyl zinc ($Ph_2NZnEt$) was also effective.

The ratio of metal compound to ligand used for formation of the catalyst is in the range of 1:1 (Tables 2–5 below) to 2:1 (Tables 1 and 6 below). When ratios less than 2:1 are used, it is likely that excess ligand is present in the catalyst solution.

The catalyst is preferably formed in an aprotic and non-complexing solvent, such as, for example, THF, ether, acetone, toluene, other hydrocarbon solvents, chlorinated solvents, or a mixture thereof. Such solvents are generally suitable for carrying out the aldol reaction as well; therefore, a catalyst solution can be prepared and used directly, as described in the Examples below. For nitroaldol reactions, ether-based solvents such as THF, dioxane, DME and diethyl ether are preferred.

Typically, the catalyst is formed by combining a 1:1 to 2:1 ratio of metal compound and ligand in solution. (See e.g. Examples 14A, 15, 17–18 and 20A.) A portion of the resulting solution is combined with the remaining reaction components, as described in the Examples below. Assuming a ratio of two metal atoms per ligand in the complex, the molar quantity of catalytic complex present in the reaction mixture would be one half the number of moles of metal compound.

III. Stereoselective Aldol Reactions

As demonstrated below, use of the catalytic complexes and methods of the invention give aldol reaction products with high enantioselectivity starting from a variety of aldehyde substrates, including substrates with no branching and/or with unsaturation at the α-carbon, which have historically given poor enantioselectivity in asymmetric addition reactions. In general, the aldehyde is of the formula RCHO, where R is selected from the group consisting of alkyl, cycloalkyl, alkenyl, alkynyl, aryl, aralkyl, aralkenyl, and aralkynyl. R is optionally substituted, where preferred substituents are selected from alkoxy, aryloxy, hydroxy, alkyl- or arylsulfonyl, sulfonamide, ester, amide, cyano, nitro, and halogen. While α-branched aldehydes typically give greater selectivity, the reaction is also successful with unbranched aldehydes, as shown below. A further advantage of the present invention is that the donor compound (nitroalkyl or ketone) need not be provided in preactivated form.

A. Reactions with Ketone Donors

A large range of ketone donors may be used, as long as an α-hydrogen is present. The ketone is preferably of the formula R'(C=O)CH$_2$Y, where Y is selected from hydrogen, hydroxy, alkoxy, aryloxy, amide, ester, alkyl- or arylsulfonyl, sulfonamide, halogen, aryl, and alkyl, and R' is selected from alkyl, cycloalkyl, alkenyl, alkynyl, aryl, aralkyl, aralkenyl, and aralkynyl. R' is optionally substituted, with preferred substituents selected from alkoxy, aryloxy, hydroxy, amide, alkyl- or arylsulfonyl, sulfonamide, ester, cyano, nitro, and halogen. In selected embodiments, Y is selected from hydrogen and hydroxyl, and R' is selected from aryl, alkenyl, alkynyl, aralkenyl, and aralkynyl. Examples include aryl methyl ketones and aryl (hydroxymethyl) ketones.

The reactions can be performed over a wide temperature range; in general, lower temperatures are expected to provide greater selectivity but require longer reaction times. Temperatures of −35° C. to room temperature were found to be generally suitable, though temperatures outside this range can also be used.

A variety of solvents were found satisfactory, including those useful for forming the catalyst, as noted above (e.g. THF, ether, acetone, toluene, other hydrocarbon solvents, and chlorinated solvents) as well as DMSO, DMF, and the protic solvent EPA (isopropanol). Addition of small amounts of EPA to reactions carried out in THF was found to increase rate and yield.

It was found that turnover frequency was generally improved by the addition of a small quantity of molecular sieves; e.g. about 50–500 mg, preferably about 100–200 mg, per mmol of aldehyde. Pore size of the molecular sieves can vary, e.g. from about 3 to 6 Angstroms, as long as the sieves are effective to trap water without trapping any significant amount of larger reaction components. In certain cases, the addition of about 5 to 15 mole % of a weak coordinating agent for zinc, such as a trialkyl phosphate, triarylphosphine oxide or triarylphosphine sulfide, was shown to improve both turnover and e.e.

Table 1 shows the results of a series of reactions employing a variety of aldehydes and ketones, and using the following reaction conditions (see general procedure in Example 14): ca. 5 mol % ligand 1a, ca. 10 mol % ZnEt$_2$, 15 mol % triphenylphosphine sulfide (Ph$_3$P=S), and 4A molecular sieves (200 mg/mmol aldehyde) in THF. Reaction time was 2 days, with the exception of entry 7 (4 days).

Absolute configurations were assigned by comparison to the literature (see characterization data in Examples below) or by analogy. Enantiomeric excess was determined using chiral HPLC (Chiracel™ OD column).

TABLE 1

Enantioselective Aldol Reactions of Aryl Methyl Ketones

| Entry No. | RCHO | Ketone Ar | Ketone:RCHO | Temp, °C | Product | Yield, % (e.e., %) |
|---|---|---|---|---|---|---|
| 1a | propyl | —Ph | 10 | −5 | 1-hydroxy-1-phenylpentan-3-one | 33(56) |
| 1b | propyl | —Ph | 10 | −15 | | 24(74) |
| 2 | isobutyl | —Ph | 10 | −5 | | 49(68) |
| 3 | isopropyl | —Ph | 10 | 5 | | 62(98) |

TABLE 1-continued

Enantioselective Aldol Reactions of Aryl Methyl Ketones

RCHO + CH₃C(O)Ar → (with 5 mol% ligand 1a, 10 mol% Et₂Zn, 15 mol% Ph₃P=S, molecular sieves 4A in THF) → R-CH(OH)-CH₂-C(O)-Ar

| Entry No. | RCHO | Ar (ketone) | Ketone:RCHO | Temp, °C | Product | Yield, % (e.e., %) |
|---|---|---|---|---|---|---|
| 4 | cyclohexyl-CH | —Ph | 10 | 5 | cyclohexyl-CH(OH)-CH₂-C(O)-Ph | 60(98) |
| 5 | Ph₂CH- | —Ph | 10 | 5 | Ph₂CH-CH(OH)-CH₂-C(O)-Ph | 79(99) |
| 6 | Ph-CH(vinyl)- | —Ph | 10 | 5 | Ph-CH(vinyl)-CH(OH)-CH₂-C(O)-Ph | 67(94 major; 98 minor) |
| 7 | TBSO-CH₂-C(CH₃)₂- | —Ph | 10 | 5 | TBSO-CH₂-C(CH₃)₂-CH(OH)-CH₂-C(O)-Ph | 61(93) |
| 8 | iPr- | 2-furyl | 10 | 5 | iPr-CH(OH)-CH₂-C(O)-(2-furyl) | 66(97) |
| 9 | iPr- | 2-MeO-C₆H₄- | 10 | 5 | iPr-CH(OH)-CH₂-C(O)-(2-MeO-C₆H₄) | 48(97) |
| 10 | iPr- | 4-MeO-C₆H₄- | 5 | 5 | iPr-CH(OH)-CH₂-C(O)-(4-MeO-C₆H₄) | 36(98) |
| 11 | iPr- | 2-naphthyl | 5 | 5 | iPr-CH(OH)-CH₂-C(O)-(2-naphthyl) | 40(96) |

Lower ketone/aldehyde ratios generally gave good selectivity but lower yields. A 96% recovery of excess acetophenone was demonstrated for entry 3.

Improved e.e.'s were obtained on aldehydes without branch points at the α-carbon by reducing the temperature of the reaction. In the remaining reactions, as can be seen, very high e.e.'s were routinely obtained. Using a chiral but racemic aldehyde, 2-phenylpropenal (entry 6), a 2:1 diastereomeric mixture of adducts, both having high e.e., was obtained.

Table 2 shows results of reaction of a less sterically demanding ketone, acetone, with various aldehydes. The reactions shown in Table 2 were performed with both ligands 1a and 1m (in which the 4-methyl phenol of 1a is replaced with 3,5-dimethyl phenol). Standard conditions were 0.5 mmol aldehyde, 0.5 ml (approx. 6.8 mmol) acetone, 100 mg 4 Å molecular sieves, a reaction temperature of 5° C., and catalyst added as a 0.1 M solution in THF. (See Example 1) In certain reactions, 5 eq of PPh$_3$S per eq of catalyst were added, as indicated.

TABLE 2

Enantioselective Aldol Reactions of Acetone with Various Aldehydes

| Entry | Aldehyde | Ligand | Mol % catalyst; additive | Product | Ratio elim:aldol | Yield aldol (%) | e.e. (%) |
|---|---|---|---|---|---|---|---|
| 1 | cyclohexanecarboxaldehyde | 1a | 5 | | 0 | 62 | 87 |
|   |   | 1m | 10 | | 0 | 85 | 93 |
|   |   |    | 10 | | 0 | 89 | 92 |
| 2 | isobutyraldehyde | 1a | 5 | | 0 | 80 | 87 |
|   |   | 1m | 10 | | 0 | 89 | 91 |
| 3 | pivaldehyde | 1a | 5 | | 0 | 76 | 86 |
|   |   | 1m | 10 | | 0 | 72 | 94 |
| 4 | diphenylacetaldehyde | 1a | 5 | | 0 | 79 | 82 |
|   |   | 1a | 10 | | 0 | 72 | 87 |
|   |   | 1m | 10 | | 0 | 84 | 91 |
| 5 | isovaleraldehyde | 1a | 5 | | 0 | 24 | 76 |
|   |   | 1m | 10 | | 0 | 59 | 84 |
| 6 | hydrocinnamaldehyde | 1a | 5 | | 1:6 | 59 | 89 |
|   |   | 1a | 10 | | 3:1 | 24 | 89 |
|   |   | 1m | 10 | | 1:15 | 76 | 82 |
| 7 | valeraldehyde | 1a | 5 | | 0 | 56 | 84 |
|   |   | 1a | 5; 5 eq PPh$_3$S | | 1:15 | 55 | 87 |
|   |   | 1m | 10 | | 0 | 69 | 89 |
|   |   | 1m | 10; 5 eq PPh$_3$S | | 0 | 72 | 84 |
| 8 | benzaldehyde | 1a | 5 | | 1:3 | 55 | 88 |
|   |   | 1a | 5; 5 eq PPh$_3$S | | 1:3 | 57 | 85 |
|   |   | 1m | 5 | | 0 | 78 | 83 |
|   |   | 1m | 10 | | 4:1 | (82) 12 | 79 |
| 9 | p-nitrobenzaldehyde | 1a | 5 | | 1:2 | 36 | 74 |
|   |   | 1a | 5 | | 0 | 62 | 78 |
|   |   | 1m | 10 | | 1:8 | (80) 54 | 76 |

Yields are isolated yields, with conversions given in parentheses. Product ratios were determined by $^1$H NMR spectroscopy of the crude product, and e.e.'s by chiral HPLC using chiracell OD or OJ columns. Absolute configurations were assigned by comparison to the literature or by analogy. (See characterizing data in Examples, below.)

With the exception of entry 1, somewhat improved results were obtained using ligand 1m over 1a under otherwise identical conditions. For an α-branched aldehyde (entry 4), a slight improvement in yield and a significant improvement in e.e. was obtained. In the difficult cases of a-unbranched and aryl aldehydes, significant improvements arose using ligand 1m. In all cases (entries 5–9), improvements in yields were obtained, frequently due to a decrease in the elimination side product. In some cases, notably entry 5, e.e. was also higher with ligand 1m.

Enantioselectivities observed in reaction of branched aldehydes with acetophenone were higher than those shown in Table 2 for acetone. For example, e.e.'s for the reaction products of the aldehydes of entries 1, 2, and 4 with acetophenone were 98–99%. Absolute configurations were the same for the acetone and acetophenone reaction products.

For α-unbranched aldehyde substrates, the catalysts derived from reaction of ligand 1 a or 1m with 2 eq of diethylzinc give the best recorded results to date. In comparative reactions using proline as the chiral auxiliary, the unbranched aldehydes shown in Table 2 gave aldol products in yields and e.e.'s ranging from 22–35% and 36–73%, respectively. Reactions using ligand 1m, in contrast, gave yields-and e.e.'s from 59–76% and 82–89%, respectively. The results are also considerably improved over the use of Ipc-X (Ipc=isopinocampheyl; X=Cl or OSO$_2$CF$_3$) as a chiral auxiliary, which must be used in stoichiometric quantities (Ramachandran et al.; Paterson et al.).

Methyl vinyl ketone has been recognized as a useful building block in organic synthesis. Therefore, the aldol reaction of MVK as a nucleophile was also examined, using a zinc complex of ligand 1a as catalyst. The reaction employed 0.5 mmol cyclohexane carboxaldehyde and ca. 10 mol % ligand/10 mol % metal (see Example 16). Products with high enantiomeric excess were obtained, as shown. Dehydration of the aldol product, however, decreased the yields.

TABLE 3

Enantioselective Aldol Reaction of MVK with Cylohexanecarboxaldehyde

| Entry | MVK, mL | Additive, mL | Solvent | Temp, °C. | Time | Yield, % | e.e., % |
|---|---|---|---|---|---|---|---|
| 1 | 0.5 | none | THF | 0 | 4h | 34 | 91 |
| 2 | 0.21 | IPA, 0.2 | THF | 0 | 3h | 20 | 90 |
| 3 | 0.5 | IPA, 0.2 | THF | 0 | 4h | 37 | 90 |
| 4 | 0.5 | MS 4A, 100 mg IPA, 0.2 | THF | 0 | 4h | 37 | 91 |
| 5 | 0.5 | MS 4A, 100 mg IPA, 0.2 | THF | −25 | 2d | 35 | 90 |
| 6 | 1 | MS 4A, 100 mg IPA, 0.2 | MVK | −25 | 2d | 65 | 94 |

Reactions of acetone and MVK as ketone donors were also conducted using different chiral ligands. The results are shown in Table 4. The aldehyde substrate in these reactions was cyclohexanecarboxaldehyde (0.5 mmol). They also employed ca. 10 mol % chiral ligand/10 mol % metal (see Example 17). The reactions of entries 9 and 10 employed 100 mg of 4A molecular sieves (MS).

TABLE 4

Enantioselective Aldol Reactions of Acetone and MVK using Various Ligands

| Entry | Ligand | Ketone, mL | Additive, mL | Solvent | Temp, °C. | Time | Yield, % | e.e., % |
|---|---|---|---|---|---|---|---|---|
| 1 | 1b | acetone, 1.5 | none | acetone | 0 | 15 h | 39 | 45 |
| 2 | 1b | acetone, 1 | IPA, 0.5 | acetone | 0 | 15 h | 74 | 40 |
| 3 | 1c | acetone, 1 | IPA, 0.5 | acetone | 0 | 15 h | 47 | 60 |
| 4 | 1c | MVK, 1 | IPA, 0.5 | MVK | 0 | 15 h | 52 | 80 |
| 5 | 1g | acetone, 1 | IPA, 0.5 | acetone | 0 | 3 d | 28 | 35 |
| 6 | 1h | MVK, 1.3 | IPA, 0.2 | MVK | −30 | 3 d | 57 | 73 |
| 7 | 1j | acetone, 0.5 | IPA, 0.2 | THF | r.t. | 18 h | 14 | 53 |
| 8 | 1k | acetone, 0.5 | 4A MS IPA, 0.2 | THF | 0 | 4 h | 59 | 72 |
| 9 | 1k | MVK, 1.3 | IPA, 0.2 | MVK | −30 | 4 d | 44 | 82 |
| 10 | 1m | acetone, 0.5 | 4A MS Ph$_3$P = S, 15% | THF | −8 | 2 d | 48 | 86 |

In this series of reactions, ligands 1c and 1m gave the highest e.e.'s at moderate temperatures. Reactions with ligands based on p-cresol, similar to 1a, but having larger aryl group on the tertiary alcohol groups, gave results similar to or somewhat superior to those using 1a. These ligands include naphthyl ligands 1c–d and biphenyl ligand 1e (data not shown for 1d–1e).

See also section B3, below, for further discussion of variations in ligand structure.

Traditionally, α-hydroxyketones have been particularly interesting synthetic subunits, due to the desirability of the polyoxygenated products, but they have presented serious chemoselectivity problems in aldol reactions. Reactions using the present catalysts, however, were very effective, giving high yields and e.e.'s in asymmetric aldol reactions with a wide range of aldehydes, including branched and non-branched. These reactions also gave high yields from nearly stoichiometric ketone/aldehyde ratios. Surprisingly, the enantiofacial selectivity with respect to the aldehyde was opposite to that observed with the methyl ketones, above (Table 1).

Table 5 shows results of the reaction of hydroxyacetophenone and cyclohexane carboxaldehyde, in a 1.5:1 molar ratio, in the presence of 2.5 to 5 mole % catalyst (prepared by reacting equimolar amounts of ligand 1a and diethylzinc in THF). Reactions were run on a 0.5 mmol scale at 0.3M aldehyde, in the presence of 100 mg 4A molecular sieves and 15 mole % Ph₃PS.

The reaction gave a high yield of the desired aldol product, with high diastereoselectivity, favoring the syn adduct as shown (d.r.=diastereomeric ratio). Lowering reaction temperature improved e.e. dramatically. In contrast to results observed with acetophenone, the presence or absence of Ph$_3$PS at −35° C. had no effect (entries 6–7).

Diastereomeric ratio (dr) was largely invariant with respect to temperature. However, it was found, remarkably, that lowering the catalyst load to 2.5 mol % (entry 8) gave a significant increase in diastereoselectivity with no appreciable loss in yield.

The relative and absolute stereochemistry of the major diastereomer was established by comparison to the product as derived from an asymmetric dihydroxylation (see Example 15). Strikingly, the absolute configuration of the stereocenter derived from the aldehyde is opposite to that obtained using acetophenone as donor.

TABLE 5

Enantioselective Aldol Reaction of α-Hydroxyacetophenone

| Entry | Mol % catalyst | 15 mol % Ph$_3$PS | Temp, ° C. | Time (h) | Isolated Yield (%) | d.r. | e.e. (%) |
|---|---|---|---|---|---|---|---|
| 1 | 5.0 | yes | r.t. | 48 | >90 | 5:1 | 30 |
| 2 | 5.0 | yes | 5 | 15 | 82 | 5:1 | 45 |
| 3 | 5.0 | yes | −5 | 48 | >90 | 5:1 | 76 |
| 4 | 5.0 | yes | −25 | 48 | >90 | 5:1 | 88 |

TABLE 5-continued

Enantioselective Aldol Reaction of α-Hydroxyacetophenone

| Entry | Mol % catalyst | 15 mol % Ph$_3$PS | Temp, ° C. | Time (h) | Isolated Yield (%) | d.r. | e.e. (%) |
|---|---|---|---|---|---|---|---|
| 5 | 5.0 | yes | −35 | 24 | 94 | 5:1 | 90 |
| 6 | 5.0 | no | −35 | 24 | 97 | 5:1 | 90 |
| 7 | 5.0 | no | −55 | 48 | 77 | 5:1 | 93 |
| 8 | 2.5 | no | −40 | 24 | 83 | 30:1 | 92 |

Table 6 illustrates the versatility of this reaction using a variety of aldehyde substrates. Reactions were run on a 0.5 mmol scale at 0.3M aldehyde, in the presence of 2.5 to 5 mole % catalyst (prepared as described in Example 18) and 100 mg 4A molecular sieves. Reactions were carried out at −35° C. for 24 h, unless otherwise indicated. The reaction of entry 6 was carried out at −55° C. Yields are isolated yields.

Notably, the reaction gave high e.e.'s from unbranched substrates (entries 5–8 and 10).

Decreasing the temperature (entry 6) gave an increase in e.e., as well as diastereoselectivity. Reactions with 2-hydroxyacetylfuran as the donor ketone also gave excellent results (entries 9 and 10).

Reducing the ratio of substrates from 1.5:1 to 1.3:1 (entries 9a and 10) had no deleterious effect on conversion or chemoselectivity. As shown in entry 2a vs. 2b, reducing this ratio further to 1.1:1.0 decreased conversion, but both the diastereoselectivity and enantioselectivity increased. A similar trend was observed with 3-methylbutanal (entry 4a vs. 4b).

In all cases examined (entries 1–5), dropping the catalyst load from 5 to 2.5 mol % increased diastereoselectivity and, in some cases (entries 2–4), e.e. significantly.

TABLE 6

Enantioselective Aldol Reactions of α-Hydroxyketones with Various Aldehydes

| | R | Ar | Ketone: RCHO | Mol % cat | Major product | Yield (%) | d.r. | e.e. (%) |
|---|---|---|---|---|---|---|---|---|
| 1 | cyclohexyl | Ph | 1.5 | 2.5 | | 83 | 30:1 | 92 |
| | | | | 5.0 | | 97 | 5:1 | 90 |

TABLE 6-continued

Enantioselective Aldol Reactions of α-Hydroxyketones with Various Aldehydes

| | R | Ar | Ketone:RCHO | Mol % cat | Major product | Yield (%) | d.r. | e.e. (%) |
|---|---|---|---|---|---|---|---|---|
| 2a | isobutyl | Ph | 1.5 | 2.5 | | 89 | 13:1 | 93 |
| 2b | | | 1.1 | 5.0 | | 93 | 5:1 | 86 |
| | | | | 5.0 | | 72 | 6:1 | 93 |
| 3 | CHPh₂ | Ph | 1.5 | 2.5 | | 74 | one product 13:1 | 96 |
| | | | | 5.0 | | 97 | | 81 |
| 4a | isobutyl (CH₂) | Ph | 1.5 | 2.5 | | 65 | 35:1 | 94 |
| 4b | | | 1.1 | 5.0 | | 96 | 3:1 | 88 |
| | | | | 5.0 | | 79 | 4:1 | 93 |
| 5a | PhCH₂CH₂ | Ph | 1.5 | 2.5 | | 78 | 9:1 | 91 |
| 5b | | | 1.1 | 5.0 | | 98 | 3:1 | 90 |
| 6 | PhCH₂CH₂ | Ph | 1.5 | 5.0 | | 62 | 3.5:1 | 96 |
| 7 | n-pentyl | Ph | 1.5 | 5.0 | | 89 | 5:1 | 86 |
| 8 | CH₂=CH(CH₂)₆ | Ph | 1.5 | 5.0 | | 91 | 5:1 | 87 |
| 9a | cyclohexyl | 2-furyl | 1.3 | 5.0 | | 90 | 6:1 | 96 |
| 9b | | | 1.5 | | | 77 | 6:1 | 98 |
| 10 | PhCH₂CH₂ | 2-furyl | 1.3 | 5.0 | | 97 | 3.4:1 | 95 |

An advantage of the asymmetric aldol reaction over asymmetric dihydroxylation in producing chiral 1,2-diols is the formation of both stereocenters simultaneous with carbon-carbon bond formation. Further, in an asymmetric dihydroxylation, chemoselectivity issues could arise with olefinic substrates, such as that of Table 3, entry The reaction described above approaches the ideal atom economical version of the asymmetric aldol reaction, employing near-stoichiometric amounts of substrate and donor and catalytic amounts of other reagents. Excellent conversion and chemoselectivity was observed with ketone/aldehyde ratios as low as 1.1:1.0.

B. Nitroalkyl Donors (Nitroaldol or Henry Reaction)

The nitroaldol reaction provides a method of forming a carbon-carbon bond under relatively mild conditions with the concomitant formation of two asymmetric centers. The resulting β-nitroalcohol product is amenable to further transformation to additional useful structures, e.g. by reduction of the nitro group, oxidation of the alcohol, etc. In accordance with the present invention, the nitroaldol reaction can be carried out between an aldehyde and a nitroalkyl compound with high stereoselectivity.

As noted above, a "nitroalkyl" compound refers to a compound which contains a nitromethyl ($-CH_2NO_2$) or nitromethylene ($>CHNO_2$) moiety and is able to form a stable carbanion on abstraction of an α-hydrogen, the simplest example being nitromethane ($CH_3NO_2$). Nitroaldol reactions can also been carried out on nitroalkyl compounds which include other functional groups, such as alcohols, ethers, including acetals and ketals, thioethers, ketones, esters, including α- and β-esters, acyloxy groups, amines, amides, and imides (see the 2001 review article by Luzzio, cited above). Such substrates are expected to be suitable for the reactions described herein, keeping in mind that when α-branching is present (i.e. a nitromethylene compound), mixtures of diastereomers may be formed.

1. Reaction Parameters

Table 7 shows the results of a series of reactions of cyclohexane carboxaldehyde with nitromethane using catalyst 1a. A 0.1M catalyst solution, which may be prepared as described in Example 20A, was added directly to the reaction solution containing nitromethane and the aldehyde substrate. All reactions were run on a 1 mmol scale at 0.33 M in aldehyde in the solvent shown, containing about 100 mg of 4A molecular sieves per 1 mmol of aldehyde. Reactions were carried out for 24 hrs (see Example 20B). Enantiomeric excess of the products was determined by chiral HPLC.

TABLE 7

Nitro Aldol Reaction between Nitromethane and Cyclohexanecarboxaldehyde

| Entry | eq. $CH_3NO_2$ | Mol % catalyst | Temp, °C. | Solvent | Yield %/ee % |
|---|---|---|---|---|---|
| 1 | 10 | 5 | 5 | THF | 69/78 |
| 2 | 10 | 5 | −20 | THF | 68/85 |
| 3 | 10 | 5 | −20 | Toluene | 68/57 |
| 4 | 10 | 5 | −20 | $CH_2Cl_2$ | 75/51 |
| 5 | 2 | 5 | −20 | $Et_2O$ | 20/55 |
| 6 | 2 | 5 | −20 | THF/dioxane, 4:1 | 17/86 |
| 7 | 10 | 5 | −78 then −20 | THF | 75/85 |
| 8 | 10 | 2.5 | −78 then −20 | THF | 44/85 |
| 9 | 6 | 5 | −78 then −20 | THF | 70/86 |

While only small amounts of catalyst (e.g. 2.5 mole %, entry 8) were effective to give high e.e.'s, about 5 mole % catalyst, along with about 5 equivalents of the nitroalkyl compound relative to aldehyde, were needed to give high conversions. In the cases where low yields were obtained (entries 5, 6 and 8), the aldehyde was recovered unchanged.

While moderate enantioselectivity was obtained at 5° C., significant improvements were seen upon lowering the temperature. Preferably, the reaction mixture is cooled at −78° C. during addition of the catalyst (entries 7–9), and the reaction allowed to proceed at a temperature of about −60° C. to −20° C. In similar reactions run with isopropyl and pivalyl aldehyde, an absolute increase in e.e. of 5% was seen in both cases on going from a reaction temperature of −25° C. to −60° C. (isopropyl 83% to 88%; pivalyl 88% to 93%).

A clear benefit was also observed from the use of coordinating polar solvents such as THF, DME and dioxane.

2. Aldehyde Substrate

As shown in Table 8, the reaction is effective for conventionally challenging substrates such as α-unbranched and α,β-unsaturated aldehydes. All reactions in the Table were carried out on a 1 mmol (aldehyde) scale, using 5 mol % catalyst (prepared from ligand 1a, as described in Example 20A) and 10 eq. $CH_3NO_2$ in 0.33 M THF solution, containing about 100 mg of 4A molecular sieves per 1 mmol of aldehyde (RCHO), at −35° C. for 24 hr, unless noted otherwise.

TABLE 8

Enantioselective Nitroaldol Reactions of Various Aldehydes with $CH_3NO_2$

| Entry | R | Product | Yield (%) | ee (%) |
|---|---|---|---|---|
| 1 | isopropyl | 3-methyl-1-nitro-2-butanol | 58 | 88 |
| 2 | tert-butyl | 3,3-dimethyl-1-nitro-2-butanol | 88 | 93 |
| 3 | PhCH₂CH₂CH(OH)CH₂NO₂ group | 3-ethyl derivative | 90 | 92 |
| 4 | 3-pentyl | 4-methyl-1-nitro-2-pentanol | 84 | 87 |
| 5a | PhCH₂CH₂CH₂– | Ph(CH₂)₃CH(OH)CH₂NO₂ | 56 | 85 |
| 5b | | | 59 | 84 |
| 6 | BnOCH₂CH₂– | BnO(CH₂)₂CH(OH)CH₂NO₂ | 56 | 86 |
| 7 | citronellyl | citronellyl nitroaldol | 81 | dr. = 19:1 |
| 8 | phenyl | 1-phenyl-2-nitroethanol | 75 | 91 |
| 9 | 1-naphthyl | 1-(1-naphthyl)-2-nitroethanol | 71 | 93 |
| 10 | 3,4-dimethoxyphenyl | 1-(3,4-dimethoxyphenyl)-2-nitroethanol | 69 | 78 |

TABLE 8-continued

Enantioselective Nitroaldol Reactions of Various Aldehydes with CH₃NO₂

| Entry | R | Product | Yield (%) | ee (%) |
|---|---|---|---|---|
| 11 | Boc-pyrrole | Boc-pyrrole-CH(OH)CH₂NO₂ | 79 | 90 |

Enantiomeric excess was determined by chiral HPLC. The e.e. of the product of entry 5 was increased to 96% by one recrystallization. Absolute stereochemistry of the products was determined by comparison to literature values and/or by NMR analysis of the (S)—O-methylmandelate derivatives (see e.g. Example 21).

α-Branched aldehydes gave nitro aldol products in high yields and e.e. (entries 1–3). Entries 1–2 were carried out at −60° C., using only 5 eq. CH₃NO₂.

Reasonable yields were obtained from α-unbranched aldehydes by increasing the nitroalkane/adhehyde equivalent ratio to 15 and by performing the reaction using more concentrated solutions (entries 5 and 6). Reaction 5a was performed using 15 eq. CH₃NO₂ and 5 mol % catalyst in 0.66 M THF solution for 2 days; reactions 5b and 6 were performed using 15 eq. CH₃NO₂ and 10 mol % catalyst in 0.33 M THF solution for 2 days.

Enantiomerically pure (R)-citronellal (entry 7) gave the nitro aldol product in high yield and high diastereomeric ratio. However, (S)-citronellal gave the corresponding product (not shown) in 51% yield and 9.6:1 diastereomeric ratio. Aromatic and heterocyclic aldehydes gave nitro aldol products in good yields and good e.e. as well (entries 8–11).

3. Ligand Variations

The reaction of Entry 10 in Table 8 was also carried out with catalysts prepared from different ligands. When the 4-methyl group of ligand 1a was replaced with fluorine, an increase in e.e. to 85% was observed. Similar increases were observed when the phenyl groups on the diaryl carbinol moieties of 1a were replaced with 4-fluorophenyl, p-biphenyl, or 2-naphthyl.

4. Further Reactions

The catalyst system reported herein allows efficient and atom economical access to enantiomerically enriched α-hydroxy amines and α-hydroxy acids which are important building blocks in organic synthesis.

The product of entry 6 is a useful bifunctional molecule that could serve, for example, as starting material for the rapid production of "GABOB" (γ-amino-β-hydroxy butyric acid). The product of entry 10 could be used as starting material for the synthesis of arbutamine.

The nitro aldol products can also be further elaborated into chiral α-hydroxy acids (Matt el al.) without epimerization of the stereogenic center (see below and Examples 22–23).

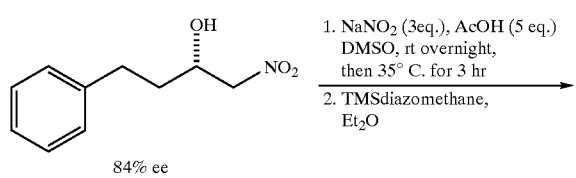

84% ee

1. NaNO₂ (3eq.), AcOH (5 eq.) DMSO, rt overnight, then 35° C. for 3 hr
2. TMSdiazomethane, Et₂O

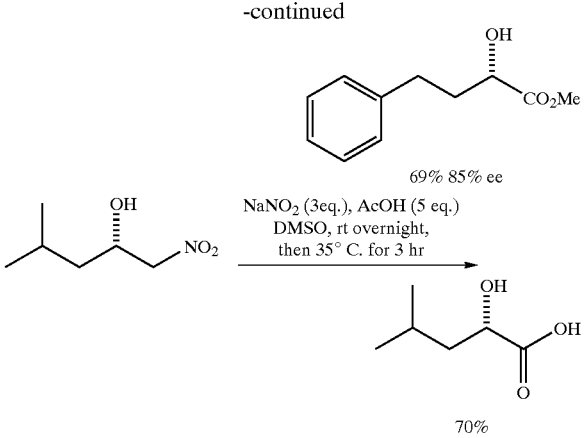

69% 85% ee

NaNO₂ (3eq.), AcOH (5 eq.) DMSO, rt overnight, then 35° C. for 3 hr

70%

EXAMPLES

The following examples illustrate but are not intended in any way to limit the invention.

Example 1

Synthesis of Ligand 1a

A. Synthesis of compound 2, 2,6-bis(hydroxymethyl)-p-cresol (see Van der Boom et al., *J. Am. Chem. Soc.* 1998, 120, 6531; Arnaud et al., *Tetrahedron* 1997, 53, 13757).

To a solution of p-cresol (54 g, 500 mmol) in aqueous NaOH solution (25 g of NaOH in 100 mL of water) was added a solution of 37% formaldehyde in water (108 g, 100 mL) at room temperature, and the mixture was stirred at the same temperature for 15 h. The mixture was filtered, and the precipitate was dissolved in water. Acetic acid was added to neutralize, and the precipitated crystals were filtered, washed with water and dried under vacuum (35.5 g, 211 mmol, 41%). Spectroscopic data was in good accordance with literature values.

B. Synthesis of Compound 3, 2,6-Bis(bromomethyl)-p-cresol (see Van der Boom, Above).

To compound 2 (4.1 g, 24.4 mmol) was added HBr in acetic acid (22 mL) at room temperature, and the mixture was stirred at the same temperature for 24 h. Water was added to the reaction mixture, and the mixture was filtered. The filtered solid was washed with water and dried under vacuum (5.9 g, 20 mmol, 82%). Spectroscopic data was in good accordance with literature values.

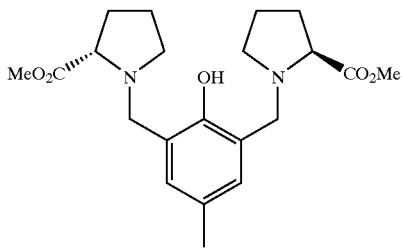

C. Synthesis of Compound 4.

To a solution of L-proline methyl ester hydrochloride (6.36 g, 38.4 mmol) and triethylamine (8.1 g, 11.2 mL, 80 mmol) in $CH_2Cl_2$ (60 mL) was added a solution of 3 (4.7 g, 16 mmol) in $CH_2Cl_2$ (20 mL) at room temperature, and the mixture was stirred at the same temperature for 24 h. The mixture was concentrated to half volume under vacuum, the residue was purified by silica gel column chromatography (pet:AcOEt, 1:1) to give 4 (5.32 g, 13.6 mmol, 85%).

IR (neat) $v$ $cm^{-1}$; 2951, 2823, 1739, 1614, 1479, 1436, 1272, 1202, 1039, 1009. $^1H$ NMR (300 MHz, $CDCl_3$) δ; 9.95 (bs, 1H), 6.85 (s, 2H), 3.96 (d, J=12.9 Hz, 2H), 3.70 (s, 6H), 3.61 (d, J=12.9 Hz, 2H), 3.28 (dd, J=8.8, 6.4 Hz, 2H), 3.06 (ddd, J=10.0, 7.1, 2.9 Hz, 2H), 2.42 (q, J=8.8 Hz, 2H), 2.21 (s, 3H), 2.20–1.72 (m, 8H). $^{13}C$ NMR (75 MHz, $CDCl_3$) δ; 174.5, 153.4, 129.5, 127.3, 122.9, 65.0, 54.3, 52.9, 51.9, 29.5, 23.1, 20.4. HRMS. Calcd for $C_{21}H_{30}N_2O_5$ ($M^+$) 390.2154, found 390.2150.

D. Synthesis of Ligand 1a.

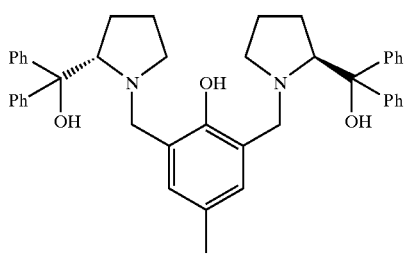

To a solution of compound 4 (6.8 g, 17.4 mmol) in THF (60 mL) was added a solution of phenylmagnesium chloride (2 M in THF, 78 mL, 156.6 mmol) at room temperature, and the mixture was stirred at the same temperature for 1 day. Sat. $NH_4Cl$ was added to the reaction mixture, and the mixture was extracted with ether. The The organic layer was washed with brine and dried over magnesium sulfate. Evaporation of the solvent under reduced pressure and purification of the residue by silica gel column chromatography (pet:AcOEt, 9:1–4:1) afforded 1a (8.2 g, 12.9 mmol, 74%). $t_r$=7.27 min (major enantiomer) and 12.50 min, (Chiralcel OD, λ=254 nm, heptane:isopropanol=80:20, 1 mL/min). $[α]_D^{25}$+49.8 (c 3.0, $CHCl_3$, 99.7% ee). IR (neat) $v$ $cm^{-1}$; 3362, 3058, 3025, 2972, 2869, 1598, 1479, 1448, 1117. $^1H$ NMR (300 MHz, $CDCl_3$) δ; 7.70 (d, J=7.6 Hz, 4H), 7.57 (d, J=7.6 Hz, 4H), 7.36–7.10 (m, 12H), 6.60 (s, 2H), 3.97 (dd, J=9.0, 4.6 Hz, 2H), 3.40 (d, J=12.7 Hz, 2H), 3.23 (d, J=12.7 Hz, 2H), 2.88–2.76 (m, 2H), 2.39 (q, J=9.5 Hz, 2H), 2.16 (s, 3H), 2.10–1.40 (m, 8H).

$^{13}C$ NMR (75 MHz, $CDCl_3$) δ; 152.6, 147.0, 146.4, 128.8, 128.2, 128.0, 127.1, 126.6, 126.4, 126.0, 125.9, 124.0, 78.9, 71.4, 57.7, 55.0, 29.6, 24.0, 20.4. MS(SIMS) 639.3 ($M^+$+1), 638.3 ($M^+$). HRMS. Calcd for $C_{30}H_{35}N2O2$ ($M^+$–$Ph_2COH$) 455.2699, found 455.2692.

Example 2

Synthesis of Ligand 1a (Alternate Route)

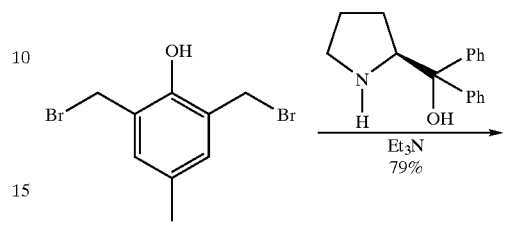

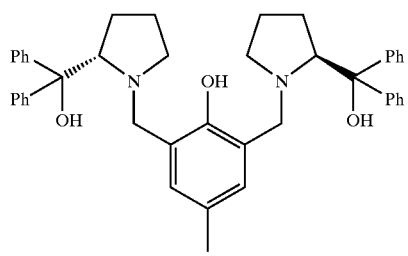

To a solution of diphenylprolinol (253 mg, 0.1 mmol) and triethylamine (0.14 mL, 1 mmol) in $CH_2Cl_2$ (2 mL) was added a solution of 3 (134 mg, 0.455 mmol) in $CH_2Cl_2$ (2 mL) at room temperature, and the mixture was stirred at the same temperature for 24 h. The mixture was concentrated to half volume under vacuum. Purification of the residue by silica gel column chromatography (pet:AcOEt, 4:1) afforded 1a (230 mg, 0.36 mmol, 79%).

Example 3

Synthesis of Ligand 1b

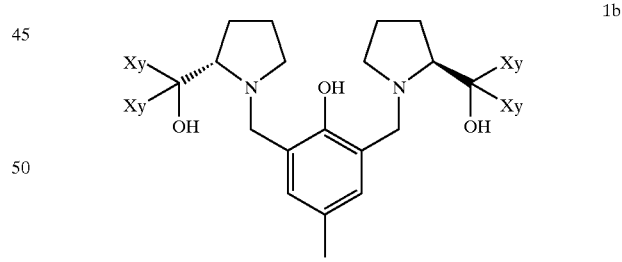

To a solution of compound 4 (500 mg, 1.28 mmol) in THF (5 mL) was added a solution of 3,5-dimethylphenylmagnesium bromide (2M in THF, 6.5 mL, 13 mmol) at room temperature, and the mixture was stirred at the same temperature for 2 days. Sat. $NH_4Cl$ was added to the reaction mixture, and the mixture was extracted with ether. The organic layer was extracted with 1N HCl, and water layer was washed with ether. Conc. $NH_4OH$ was added to the water layer, and the mixture was extracted with ether. The organic layer was washed with brine and dried over magnesium sulfate. Evaporation of the solvent under reduced pressure and purification of the residue by silica gel column chromatography (pet:AcOEt, 4:1) afforded 1b (396 mg, 0.492 mmol, 38%).

$^1$H NMR (300 MHz, CDCl$_3$) δ; 7.23 (s, 4H), 7.15 (s, 4H), 6.81 (s, 2H), 6.70 (s, 2H), 6.55 (s, 2H), 3.85 (dd, J=9.0, 4.4 Hz, 2H), 3.19 (d, J=12.9 Hz, 2H), 3.08 (d, J=12.9 Hz, 2H), 2.88–2.78 (m, 2H), 2.50–1.52 (m, 10H), 2.30 (s, 12H), 2.23 (s, 12H), 2.15 (s, 3H).

$^{13}$C NMR (75 MHz, CDCl$_3$) δ; 152.5, 147.0, 146.3, 137.4, 137.3, 128.8, 128.2, 128.0, 127.0, 124.0, 123.7, 123.6, 78.7, 71.6, 57.1, 55.2, 29.7, 24.2, 21.7, 21.6, 21.5, 20.5. MS(SIMS) 751.3 (M$^+$+1), 750.3 (M$^+$).

Example 4

Synthesis of Ligand 1c

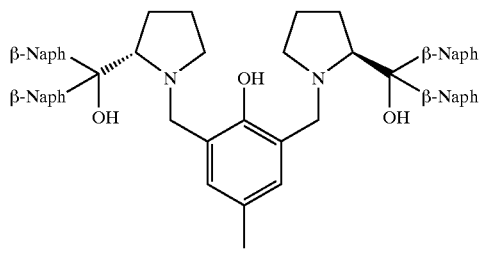

A solution of compound 4 (1 g, 2.56 mmol) in THF (5 mL) was added to a solution of β-naphthyl magnesium bromide (1M in THF, 17.9 mL, 17.9 mmol) at 0° C., and the mixture was stirred at room temperature for 15 h. Sat. NH$_4$Cl was added to the reaction mixture, and the mixture was extracted with ether. The organic layer was washed with brine and dried over magnesium sulfate. Evaporation of the solvent under reduced pressure and purification of the residue by silica gel column chromatography (pet:AcOEt, 4:1–1:1) afforded 1c (1.5 g, 1.79 mmol, 70%). IR (neat) ν cm$^{-1}$; 3346, 3056, 2972, 2870, 1949, 1914, 1740, 1628, 1599, 1478, 1269, 1122. $^1$H NMR (300 MHz, CDCl$_3$) δ; 8.41 (s, 2H), 8.14 (s, 2H), 7.98–7.32 (m, 24H), 6.45 (s, 2H), 4.19 (dd, J=9.3, 5.1 Hz, 2H), 3.39 (d, J=12.7 Hz, 2H), 3.16 (d, J=12.7 Hz, 2H), 2.82–2.72 (m, 2H), 2.37 (dt, J=9.5, 6.8 Hz, 2H), 2.16–1.55 (m, 8H), 2.03 (s, 3H). $^{13}$C NMR (75 MHz, CDCl$_3$) δ; 152.8, 144.3, 143.8, 133.2, 133.1, 128.9, 128.4, 128.3, 127.8, 127.8, 127.7, 127.4, 127.3, 126.9, 125.9, 125.7, 124.8, 124.7, 124.5, 124.4, 123.7, 79.2, 70.7, 57.6, 55.1, 29.8, 24.0, 20.2. MS(SIMS) 839.4 (M$^+$+1).

Example 5

Synthesis of N-Benzyl (S)-Proline Methyl Ester 5

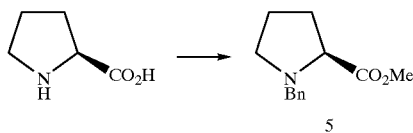

Acetylchloride (9.26 mL, 130.28 mmol) was added dropwise to a stirred and cooled (0° C.) solution of (S)-proline (5 g, 43.42 mmol) in MeOH (86 mL). After the addition, the ice bath was removed and the stirring was continued for 15 h at room temperature. The solvent was then evaporated and the residual oil redissolved in dry CH$_3$CN (70 mL). Et$_3$N (18 mL, 130 mmol) and BnBr (6.20 mL, 52.10 mmol) were added to obtain a white suspension. After 12 h of stirring at room temperature, the CH$_3$CN was evaporated, and the residue was partitioned between saturated NH$_4$Cl (200 mL) and Et$_2$O (200 mL). The phases were separated, the aqueous layer was extracted with Et2O (40 mL×2), and the combined organic phases were washed with water and brine, dried (MgSO$_4$), and concentrated. The residue was purified over silica gel using 5 to 10% EtOAc/pet ether to give a clear oil (6.37 g, 69%): $^1$H NMR (300 MHz, CDCl$_3$) δ 1.70–2.20 (m, 4H), 2.32–2.46 (m, 1H), 3.00–3.10 (m, 1H), 3.20–3.30 (m, 1H), 3.56 (d, J=12.7 Hz, 1H), 3.64 (s, 3H), 3.88 (d, J=12.7 Hz, 1H), 7.25–7.35 (m, 5H). The spectroscopic data agrees with literature values (Corey, E. J., Link, J. O.; *J. Org. Chem.* 1991, 56, 442).

Example 6

Synthesis of Ligand 1e

A. Preparation of Bis(biphenylyl)-(s)-prolinol

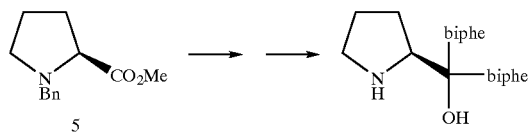

A solution of 4-bromobiphenyl (7.42 g, 31.87 mmol) in 40 mL THF was prepared, and 10 mL was added to Mg (0.85 g, 35.05 mmol) and one crystal of I$_2$ in THF (10 mL). The Grignard reaction was initiated with the aid of gentle warming by a heat gun. After the iodine color had dissipated, the remaining 30 mL of bromide solution was added dropwise to the reaction mixture. After the reflux subsided, the solution was warmed over an oil bath (70° C.), for 30 minutes, then cooled to 0° C. N-benzyl-(S)-proline methyl ester (5, 2.18 g, 9.96 mmol) in THF (10 mL) was added. After the addition, the solution was allowed to warm to room temperature and stirred for another 8 hours. Saturated NH$_4$Cl (150 mL) was added and the resulting mixture was diluted with Et$_2$O (200 mL). The phases were separated and the organic phase was washed with H$_2$O and brine, dried (MgSO$_4$), and concentrated. The residue was purified over a short silica gel column using 5 to 20% EtOAc/pet ether to a give a white solid, which was recrystalized with CH$_2$Cl$_2$/pet ether to obtain white needles (4.106 g, 83%): mp 85–86° C., $^1$H NMR (300 MHz, CDCl$_3$) δ 1.60–1.74 (m, 2H), 1.76–1.88 (m, 1H), 1.94–2.08 (m, 1H), 2.40 (dd, J=16.6, 9.0 Hz, 1H), 2.92–3.00 (m, 1H), 3.10 (d, J=12.7 Hz, 1H), 3.38 (d, J=12.5 Hz, 1H), 4.06 (dd, J=9.3, 4.6 Hz, 1H), 5.04 (s, 1H), 7.04–7.60 (m, 14H), 7.68 (d, J=8.3 Hz, 2H), 7.82 (d, J=8.3 Hz, 2H).

10% Pd/C (0.30 g) was added in one portion to a stirred solution of the N-benzyl compound (1.25 g, 2.32 mmol) and NH$_4$HCO$_2$ (0.88 g, 13.96 mmol) and EtOAc (5 mL) under Ar. After 1 hour, the suspension was filtered through a pad of Celite using MeOH as rinse. The solvent was evaporated and the residue was purified over a short silica gel column to give an off white solid (0.523 g, 56%) which was recrystalized from EtOAc/pet ether to obtain white needles: [α]$^{25}_D$-51.95 (c 7.83, CH$_2$Cl$_2$), FTIR (CH$_2$Cl$_2$ cast) 3363, 2973, 1599, 1485 cm$^{-1}$; $^1$H NMR (300 MHz, CDCl$_3$) δ 1.60–1.90 (m, 4H), 2.90–3.10 (m, 2H), 4.33 (t, J=8.2 Hz, 1H), 7.30–7.72 (m, 18H); $^{13}$C NMR (300 MHz, CDCl$_3$) δ 25.53, 26.35, 46.79, 64.54, 77.43, 125.92, 126.26, 126.75, 127.01, 127.13, 128.64, 128.69, 139.17, 139.35, 140.76, 140.87, 144.43, 147.18.

B. Synthesis of Ligand 1e.

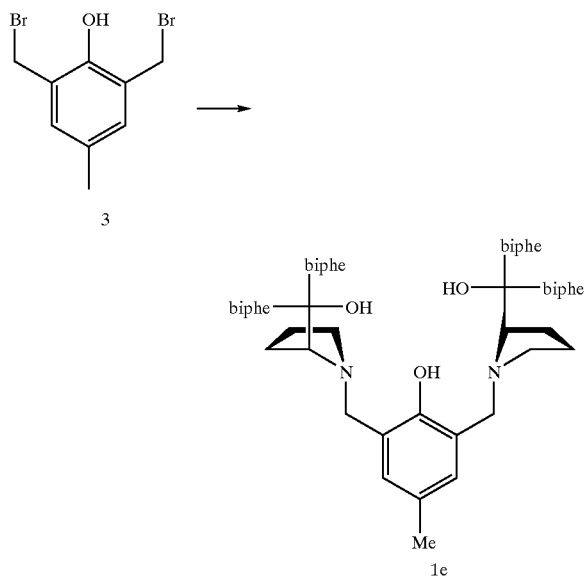

Dibromide 3 (0.175 g, 0.60 mmol) (see Example 1B) was added in one portion to a stirred and cooled (0° C.) solution of (S)-bis(biphenylyl)prolinol, above (0.51 g, 1.258 mmol) and $K_2CO_3$ (0.345 g, 2.50 mmol) in dry DMF (3 mL). The solution was allowed to warm to room temperature and stirred for 12 h. The mixture was partitioned with $Et_2O$ (50 mL) and water (30 mL). The aqueous phase was extracted with $Et_2O$ (10 mL×2) and the combined organic phases were washed with water and brine, dried ($MgSO_4$) and concentrated. The residue was purified over grade III alumina using 5 to 15% EtOAc/pet ether to give a yellow oil. The oil was redissolved in $CH_2Cl_2$ and dried over $Na_2SO4$ and the solvent was evaporated. The product was azeotroped with benzene (10 mL×2) to obtain a white powder (0.42 g, 74%): $[\alpha]^{25}_D$+86.51 (c 1.58, $CH_2Cl_2$); FTIR ($CH_2Cl_2$ cast) 3425, 1636, 1448 cm$^{-1}$; $^1$H NMR (300 MHz, CDCl$_3$) δ 1.42–1.50 (m, 4H), 1.56–1.90 (m, 2H), 1.96–2.04 (m, 2H), 2.13 (s, 3H), 2.42 (dd, J=16.1, 9.5 Hz, 2H), 2.76–2.88 (m, 2H), 3.24 (d, J=12.7 Hz, 2H), 3.58 (d, J=12.9 Hz, 2H), 4.02 (dd, J=9.0, 5.1 Hz, 2H), 6.06 (s, 2H), 7.22–7.60 (m, 12H), 7.68 (d, J=9.0 Hz, 4H), 7.82 (d, J=9.0 Hz, 4H); $^{13}$C NMR (75.5 MHz, CDCl$_3$) δ 23.86, 29.66, 54.99, 57.86, 71.25, 78.66, 124.05, 126.33, 126.42, 126.76, 126.99, 127.20, 128.59, 128.67, 129.04, 139.17, 139.35, 140.63, 140.79, 145.55, 146.21, 152.79.

Example 7

Synthesis of Ligand 1f

A. Preparation of Bis(o-tolyl)-(S)-prolinol

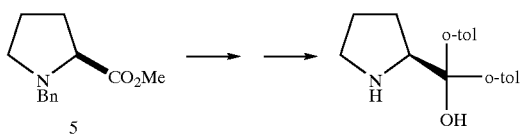

o-Tolylmagnesium bromide (7.32 mL, 1 M in THF, 7.32 mmol) was added dropwise to a stirred and cooled (0° C.) solution of ester 5 (0.617 g, 2.81 mmol) in THF (5 mL). After the addition, the resulting solution was allowed to warm to room temperature and stirred for 8 hours. Saturated $NH_4Cl$ (10 mL) was added and the mixture was partitioned with $Et_2O$ (30 mL) and water (10 mL). The organic layer was washed with water and brine, dried ($MgSO_4$), and concentrated. The residue was purified over silica gel using 5 to 10% EtOAc/pet ether to obtain an oil (0.869 g, 83%).

10% Pd/C (0.18 g) was added in one portion to a stirred solution of the above product (0.743 g, 2.00 mmol) and $NH_4HCO_2$ (1.51 g, 24.01 mmol) in MeOH (10 mL) under Ar. After 8 hours, the mixture was filtered through a pad of Celite using MeOH as rinse. The solvent was evaporated and the residue was purified by silica gel using EtOAc to give XX as an oil (0.46 g, 82%): $[\alpha]^{25}_D$–149.35 (c 1.52, $CH_2Cl_2$), FTIR ($CH_2Cl_2$ cast) 3385, 3054, 2986, 1601 cm$^{-1}$; $^1$H NMR (300 MHz, CDCl$_3$) δ 1.30–1.44 (m, 1H), 1.60–1.84 (m, 3H), 2.02 (s, 3H), 2.08 (s, 3H), 3.06 (t, J=5.93 Hz, 1H), 4.30–4.42 (m, 1H), 6.92–7.20 (m, 6H), 7.46 (d, J=7.1 Hz, 1H), 7.76 (br s, 1H); $^{13}$C NMR (75.5 MHz, CDCl$_3$) δ 21.65, 21.95, 25.56, 27.47, 46.59, 62.24, 78.85, 124.68, 124.72, 126.55, 126.60, 126.88, 128.15, 131.76, 132.80, 142.38, 144.19.

B. Synthesis of Ligand 1f.

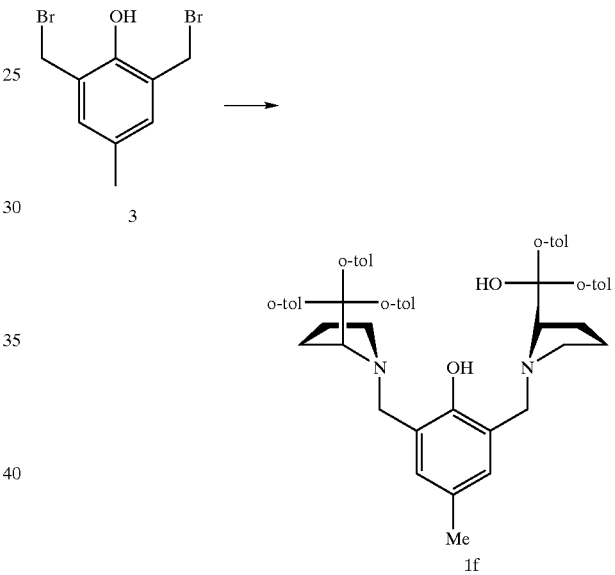

Dibromide 3 (0.262 g, 0.84 mmol) (see Example 1B) was added in one portion to a stirred and cooled (0° C.) solution of bis(o-tolyl)(S)-prolinol, above (0.494 g, 1.75 mmol) and $K_2CO_3$ (0.47 g, 3.40 mmol) in dry DMF (3 mL). The solution was stirred at room temperature for 12 h, then partitioned with $Et_2O$ (20 mL) and water (10 mL). The aqueous layer was extracted with $Et_2O$ and the combined organic phases were washed with water and brine, dried ($MgSO_4$) and concentrated. The residue was purified over grade III alumina using 5 to 10% EtOAc/pet ether to give an oil, which was redissolved in $CH_2Cl_2$ and dried over $Na_2SO_4$. After evaporation of solvent, the product was azeotroped with benzene (5 mL×2) to give a white powder (0.408 g, 69%): $[\alpha]^{25}_D$+113.54 (c 4.02, $CH_2Cl_2$); FTIR ($CH_2Cl_2$ cast) 3386, 3054, 2970, 1602 cm$^{-1}$;$^1$H NMR (300 MHz, CDCl$_3$) δ 1.56 (br s, 2H), 1.68–1.78 (m, 2H), 2.00–2.30 (m, 16H), 2.38 (dd, J=10.25, 6.3 Hz, 2H), 2.83 (br s, 2H), 3.24 (br d, J=12 Hz, 2H), 4.03 (dd, J=9.3, 2.9 Hz, 2H), 6.63 (s, 2H), 6.98–7.28 (m, 12H), 7.54 (br s, 2H), 7.92 (br s, 2H); 13C NMR (75.5 MHz, CDCl3) d 20.17, 20.70, 21.23, 21.33, 21.99, 22.11, 22.65, 22.74, 24.97, 25.06, 30.75, 55.19, 58.13, 70.50, 81.52, 123.93, 124.40, 125.78, 127.28, 127.33, 127.47, 128.25, 129.24, 129.53, 132.42, 141.85, 143.22, 152.61.

Ligand 1d was prepared in a similar manner by reaction of N-benzyl-(S)-proline methyl ester (5) with naphthyl magnesium bromide, followed by deprotection of the amine and reaction with 2,6-bis(bromomethyl)p-cresol (3).

Example 8

Synthesis of Ligand 1g

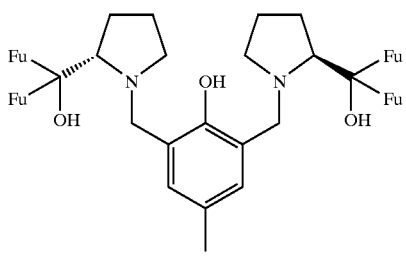

1g

A solution of n-BuLi (1.55 M in hexane, 8.3 mL, 12.8 mmol) was added to a solution of furan (1.12 mL, 15.4 mmol) in THF (20 mL) at 0° C., and the mixture was stirred at 40° C. for 3 h. A solution of compound 4 (500 mg, 1.28 mmol) in THF (5 mL) was added to the reaction mixture at 0° C., and the mixture was stirred at room temperature for 1 day. Sat. NH$_4$Cl was added to the reaction mixture, and the mixture was extracted with ether. The organic layer was washed with brine and dried over magnesium sulfate. Evaporation of the solvent under reduced pressure and purification of the residue by silica gel column chromatography (pet:AcOEt, 2:1) afforded 1g (710 mg, 1.19 mmol, 93%). IR (neat) ν cm$^{-1}$; 3385, 2971, 2823, 2810, 1612, 1480, 1381, 1150, 1007, 809. $^1$H NMR (300 MHz, CDCl$_3$) d; 7.48 (s, 2H), 7.43 (s, 2H), 6.73 (s, 2H), 6.47 (bs, 4H), 6.35 (bs, 4H), 3.90 (d, J=12.7 Hz, 2H), 3.69 (dd, J=6.8, 6.4 Hz, 2H), 3.38 (d, J=12.7 Hz, 2H), 2.72 (ddd, J=9.3, 6.6, 2.9 Hz, 2H), 2.30 (dt, J=9.8, 6.4 Hz, 2H), 2.20 (s, 3H), 1.94–1.84 (m, 4H), 1.62–1.50 (m, 2H), 1.20–1.04 (m, 2H). $^{13}$C NMR (75 MHz, CDCl$_3$) d; 155.7, 155.2, 153.3, 142.2, 141.9, 128.9, 127.0, 124.3, 110.4, 110.3, 107.9, 107.5, 74.8, 70.2, 58.6, 54.6, 27.9, 24.0, 20.4. HRMS. Calcd for C$_{35}$H$_{39}$N$_2$O$_7$ (M$^+$+H) 599.2757, found 599.2770.

Example 9

Synthesis of Ligand 1h

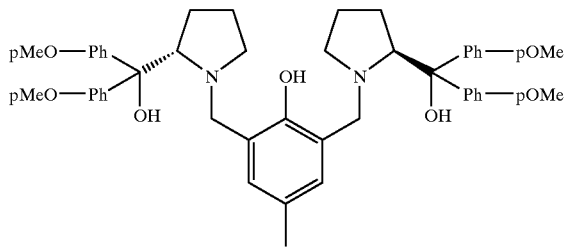

1h

A solution of p-bromoanisol (1.93 g, 1.3 mL, 10.3 mmol) in THF (2 mL) was added to a suspension of magnesium (311 mg, 12.8 mmol) in THF (2 mL) at r.t., and the and the mixture was stirred with refluxing for 30 min. A solution of compound 4 (500 mg, 1.28 mmol) in THF (4 mL) was added to the mixture, and the mixture was stirred for 18 h. Sat. NH$_4$Cl was added to the reaction mixture, and the mixture was extracted with ether. The organic layer was washed with brine and dried over magnesium sulfate. Evaporation of the solvent under reduced pressure and purification of the residue by silica gel column chromatography (pet:AcOEt, 2:1–1:1-AcOEt only) afforded 1h (373 mg, 0.492 mmol, 38%). $^1$H NMR (300 MHz, CDCl$_3$) d; 7.57 (d, J=8.8 Hz, 4H), 7.44 (d, J=8.8 Hz, 4H), 6.84 (d, J=8.8 Hz, 8H), 6.62 (s, 2H), 3.86 (dd, J=9.0, 4.6 Hz, 2H), 3.77 (s, 6H), 3.73 (s, 6H), 3.54 (d, J=12.7 Hz, 2H), 3.24 (d, J=12.7 Hz, 2H), 2.82–2.76 (m, 2H), 2.36 (td, J=9.5, 6.3 Hz, 2H), 2.16 (s, 3H), 2.05–1.91 (m, 2H), 1.84–1.72 (m, 2H), 1.66–1.52 (m, 2H), 1.50–1.36 (m, 2H). $^{13}$C NMR (75 MHz, CDCl$_3$) d; 158.0, 157.9, 152.8, 139.5, 139.0, 128.9, 127.1, 124.1, 113.5, 113.2, 78.4, 71.3, 57.9, 55.1, 55.0, 54.9, 29.6, 24.0, 20.4.

Example 10

Synthesis of Ligand 1j

A. Synthesis of compound 6 (see de Mendoza el al., *Tetrahedron* 46:671, 1990).

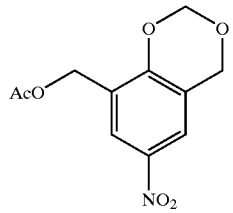

6

To a mixture of paraformaldehyde (6 g), acetic acid (25 mL), and conc. H$_2$SO$_4$ (11 mL) was added p-nitrophenol (7 g, 50 mmol) at 55° C., and the mixture was stirred at the same temperature for 2 days. Water (30 mL) was added to the reaction mixture, followed by K$_2$CO$_3$ (0.2 mol). The mixture was filtered, and the precipitate was washed with cold water. Compound 6 was recrystallized from ethanol (10.9 g, 43 mmol, 86%). Spectroscopic data was in good accordance with literature values.

B. Synthesis of 2,6-bis(bromomethyl)4-nitrophenol (see de Mendoza et al., above).

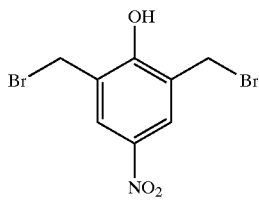

A mixture of 6 (1 g, 3.95 mmol) and 48% HBr in water (30 mL) was stirred at reflux for 15 h. The mixture was filtered at room temperature, and the precipitate was washed with cold water. The crystals were dissolved in CH$_2$Cl$_2$, and the mixture was filtered. Concentration of the filtrate under vacuum gave the title compound (820 mg, 2.52 mmol, 64%). Spectroscopic data was in good accordance with literature values.

C. Synthesis of Ligand 1j.

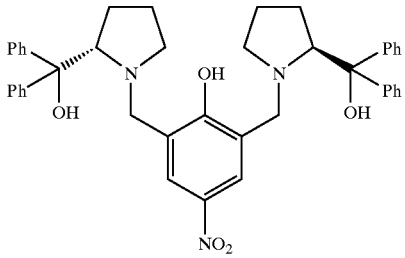

1j

To a solution of diphenylprolinol (253 mg, 0.1 mmol) and triethylamine (0.14 mL, 1 mmol) in CH$_2$Cl$_2$ (2 mL) was added a solution of 2,6-bis(bromomethyl)$_4$-nitrophenol, above (148 mg, 0.455 mmol) in CH$_2$Cl$_2$ (2 mL) at room temperature, and the mixture was stirred at the same temperature for 24 h. The mixture was concentrated to half volume under vacuum. Purification of the residue by silica gel column chromatography (pet:AcOEt, 3:1) afforded 1j (146 mg, 0.218 mmol, 48%). IR (neat) vcm$^{-1}$; 3383, 3059, 2972, 2870, 1954, 1896, 1816, 1595, 1448, 1333, 1286, 1095. $^1$H NMR (300 MHz, CDCl$_3$) d; 7.70 (s, 2H), 7.67 (d, J=7.5 Hz, 4H), 7.56 (d, J=7.5 Hz, 4H), 7.36–7.09 (m, 12H), 3.99 (dd, J=9.3, 4.9 Hz, 2H), 3.40 (d, J=13.4 Hz, 2H), 3.31 (d, J=13.4 Hz, 2H), 2.85 (ddd, J=9.5, 6.4, 3.2 Hz, 2H), 2.38 (td, J=9.5, 6.4 Hz, 2H), 2.14–2.00 (m, 2H), 1.91–1.79 (m, 2H), 1.74–1.54 (m, 4H).

Example 11

Synthesis of Ligand 1k

A. Synthesis of compound 7, 2,6-bis(hydroxymethyl)4-methoxyphenol (see Moran et al., *J. Am. Chem. Soc.* 74:127, 1952).

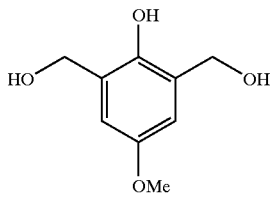

7

To a suspension of p-methoxyphenol (6.2 g, 50 mmol) in water (40 mL) was added 9.2 mL of 37% formaldehyde solution. To this mixture was added 1.6 g of calcium oxide with stirring. The mixture was stored in the dark for 5 days. The mixture was then treated with 4 mL of acetic acid, cooled at 0° C., the mixture was filtered to give compound 7 (4 g, 21.7 mmol, 43%). mp. 128° C. (lit. 127–128° C.). IR (KBr) v cm$^{-1}$; 3331, 2940, 1736, 1612, 1483, 1456, 1381, 1314, 1261, 1208, 1148, 1069. $^1$H NMR (300 MHz, acetone-d$_6$) d; 8.1 (bs, 1H), 6.74 (s, 2H), 4.73 (s, 4H), 4.64 (bs, 2H), 3.71 (s, 3H).

B. Synthesis of compound 8, 2,6-bis(bromomethyl)4-methoxyphenol (see Moran et al., above)

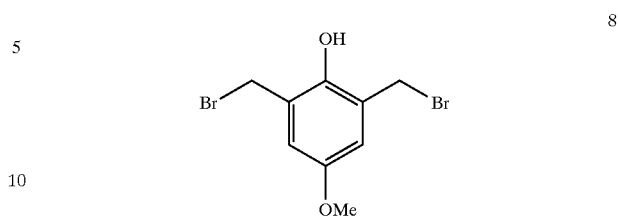

8

To a solution of HBr in acetic acid (22 mL) and acetic acid (3 mL) was added compound 7 at room temperature, and the mixture was stirred at the same temperature for 1 h. The mixture was filtered, and the filtered solid was washed with acetic acid dried under vacuum (2.8 g, 9 mmol, 83%). mp. 105° C. (lit. 113–114° C.). IR (KBr) v cm$^{-1}$; 3497, 2940, 2838, 1617, 1483, 1438, 1333, 1259, 1195, 1159, 1044, 985. $^1$H NMR (300 MHz, CDCl$_3$) δ; 6.83 (s, 2H), 5.21 (s, 1H), 4.53 (s, 4H), 3.77 (s, 3H).

C. Synthesis of Compound 9.

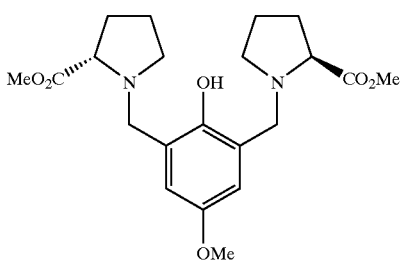

9

To a solution of L-proline methyl ester hydrochloride (900 mg, 5.43 mmol) and compound 8 (700 mg, 2.26 mmol) in CH$_2$Cl$_2$ (20 mL) was added triethylamine (1.45 g, 2 mL, 14.3 mmol) at room temperature, and the mixture was stirred at the same temperature for 3 h. The mixture was poured onto water and extracted with ether. The organic layer was washed with brine and dried over magnesium sulfate. Evaporation of the solvent under reduced pressure and purification of the residue by silica gel column chromatography (CHCl$_3$:MeOH, 10:1) afforded 9 (750 mg, 1.85 mmol, 82%). IR (neat) v cm$^{-1}$; 3352, 2952, 2836, 1740, 1611, 1479, 1378, 1272, 1204, 1054, 862. $^1$H NMR (300 MHz, CDCl$_3$) δ; 6.65 (s, 2H), 4.00 (d, J=13.2 Hz, 2H), 3.72 (s, 3H), 3.70 (s, 6H), 3.63 (d, J=13.2 Hz, 2H), 3.31 (dd, J=8.5, 5.9 Hz, 2H), 3.11–3.04 (m, 2H), 2.50–2.41 (m, 2H), 2.23–2.09 (m, 2H), 2.00–1.73 (m, 6H). $^{13}$C NMR (75 MHz, CDCl$_3$) δ; 174.2, 151.8, 149.6, 123.6, 114.4, 64.8, 55.7, 54.3, 52.9, 51.9, 29.4, 23.1.

D. Synthesis of Ligand 1k.

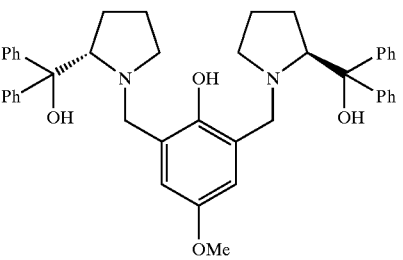

1k

To a solution of compound 9 (680 mg, 1.68 mmol) in THF (15 mL) was added a solution of phenylmagnesium chloride (2 M in THF, 6.7 mL, 13.4 mmol) at room temperature, and the mixture was stirred at the same temperature for 20 h. Sat. NH₄Cl was added to the reaction mixture, and the mixture was extracted with ether. The organic layer was washed with brine and dried over magnesium sulfate. Evaporation of the solvent under reduced pressure and purification of the residue by silica gel column chromatography (CHCl₃:MeOH, 40:1) afforded 1k (650 mg, 0.994 mmol, 59%). IR (neat) ν cm⁻¹; 3384, 3058, 3022, 2973, 2871, 1954, 1887, 1811, 1597, 1480, 1449, 1381.

¹H NMR (300 MHz, CDCl₃) δ; 7.68 (d, J=7.3 Hz, 4H), 7.55 (d, J=7.3 Hz, 4H), 7.34–7.10 (m, 12H), 6.38 (s, 2H), 3.98 (dd, J=9.3, 4.6 Hz, 2H), 3.69 (s, 3H), 3.36 (d, J=12.7 Hz, 2H), 3.26 (d, J=12.7 Hz, 2H), 2.84 (ddd, J=9.8, 6.3, 3.2 Hz, 2H), 2.41 (td, J=9.8, 6.3 Hz, 2H), 2.09–1.95 (m, 2H), 1.86–1.75 (m, 2H), 1.70–1.47 (m, 4H). ¹³C NMR (75 MHz, CDCl₃) δ; 151.6, 148.8, 146.9, 146.3, 128.2, 128.0, 126.6, 126.4, 125.9, 125.8, 124.8, 113.6, 78.9, 71.4, 57.7, 55.6, 55.1, 29.6, 24.1.

Example 12

Synthesis of Ligand 1m

A. Synthesis of compound 10, dimethyl (2-hydroxy-4,6-dimethyl) isophthalate (see Bertz, *Synthesis* 708, 1980 and Fahrni et al., *Helv. Chim. Acta* 81:491, 1998).

To a solution of 2,4-pentanedione (8.7 g, 50 mmol) was added 2.5 mL of 2N NaOH and 47.5 mL of water at room temperature, and the mixture was stirred at the same temperature for 10 min. A solution of dimethyl acetonedicarboxylate in MeOH (50 mL) was added to the reaction mixture, and the mixture was stirred at room temperature for 24 h. The mixture was filtered, and the solid was washed with water and dried under vacuum (10, 10.2 g, 42.9 mmol, 86%). Spectroscopic data was in good accordance with literature values.

B. Synthesis of compound 11, 2,6-bis(hydroxymethyl)-3,5-dimethylphenol. (See Fitzgerald, *J. Appl. Chem.* 289, 1955.)

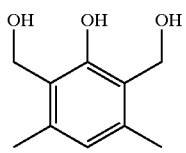

11

To a suspension of LiAlH₄ (3.7 g, 97.1 mmol) in THF (80 mL) was added a solution of 10 (7 g, 29.4 mmol) in THF (40 mL) at room temperature, and the mixture was stirred at 50° C. overnight. 1N HCl (80 mL) was added carefully to the mixture, and the mixture was extracted with AcOEt. The aqueous layer was extracted with AcOEt:THF. The combined organic layer was washed with brine and dried over magnesium sulfate. Evaporation of the solvent under reduced pressure and purification of the residue by recrystallization from AcOEt afforded 11 (4.9 g, 26.9 mmol, 92%). mp. 145° C. (lit. 142–144° C.). IR (KBr) ν cm⁻¹; 3458, 3222, 3082, 2905, 1627, 1576, 1460, 1304, 1083, 1033, 1004, 986. ¹H NMR (300 MHz, CDCl₃) d; 9.19 (s, 1H), 6.46 (s, 1H), 4.76 (s, 4H), 4.40 (s, 2H), 2.21 (s, 6H).

C. Synthesis of Compound 12, 2,6-bis(bromomethyl)4-methoxyphenol.

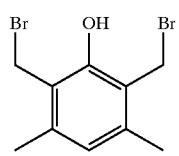

12

To a solution of compound 11 (2.1 g, 11.5 mmol) in ether (20 mL) was added 48% aqueous HBr (10 mL) at room temperature, and the mixture was stirred at the same temperature for 20 min. The mixture was poured onto water and extracted with ether. The organic layer was washed with water and brine and dried over magnesium sulfate. Evaporation of the solvent under reduced pressure gave almost pure 12 (3.4 g, 11.0 mmol, 96%). mp. 119° C. IR (KBr) ν cm⁻¹; 3538, 3472, 2926, 1619, 1572, 1448, 1306, 1254, 1208, 1148, 1040, 969. ¹H NMR (300 MHz, CDCl₃) δ; 6.68 (s, 1H), 5.41 (s, 1H), 4.62 (s, 4H), 2.36 (s, 6H). ¹³C NMR (75 MHz, CDCl₃) δ; 153.5, 138.8, 125.4, 121.4, 26.6, 18.9.

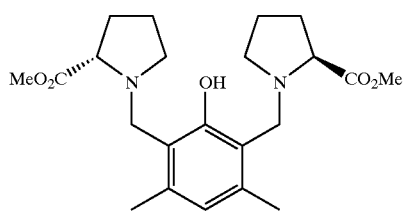

13

D. Synthesis of Compound 13.

To a solution of L-proline methyl ester hydrochloride (4.6 g, 28 mmol) and triethylamine (6.7 g, 9.2 mL, 66 mmol) in CH₂Cl₂ (60 mL) was added a solution of 12 (3.4 g, 11 mmol) in CH₂Cl₂ (40 mL) at room temperature, and the mixture was stirred at the same temperature for 18 h. The mixture was concentrated to half volume under vacuum and the residue purified by silica gel column chromatography (pet:AcOEt, 2:1) to afford 13 (2.3 g, 5.69 mmol, 52%). IR (neat) ν cm⁻¹; 2951, 2851, 1732, 1622, 1574, 1455, 1372, 1311, 1203, 1133, 1073, 1039. ¹H NMR (300 MHz, CDCl₃) δ; 10.6(s, 1H), 6.46 (s, 1H), 3.86 (d, J=13.0 Hz, 2H), 3.78 (d, J=13.0 Hz, 2H), 3.68 (s, 6H), 3.30 (dd, J=8.8, 6.1 Hz, 2H), 3.05–2.97 (m, 2H), 2.46 (q, J=8.3 Hz, 2H), 2.25 (s, 6H), 2.22–1.72 (m, 8H). ¹³C NMR (75 MHz, CDCl₃) δ; 174.5, 156.6, 136.5, 122.9, 119.4, 65.1, 52.7, 51.8, 50.1, 29.6, 23.2, 19.4. HRMS. Calcd for C22H32N2O5 (M⁺) 404.2311, found 404.2305.

E. Synthesis of Ligand 1m.

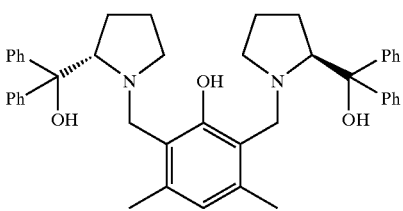

1m

To a solution of compound 13 (2.25 g, 5.57 mmol) in THF (10 mL) was added a solution of phenylmagnesium chloride (2 M in THF, 28 mL, 55.7 mmol) at room temperature, and the mixture was stirred at the same temperature for 2 days. Sat. NH$_4$Cl was added to the reaction mixture, and the mixture was extracted with ether. The organic layer was washed with brine and dried over magnesium sulfate. Evaporation of the solvent under reduced pressure and purification of the residue by silica gel column chromatography (pet:AcOEt, 4:1–2:1) afforded 1m (2.5 g, 3.83 mmol, 69%). $[\alpha]_D^{26}$+26.2 (c 1.62, CHCl$_3$). IR (neat) ν cm$^{-1}$; 3356, 3059, 3029, 2967, 2870, 1686, 1598, 1573, 1493, 1449, 1374, 1311. $^1$H NMR (300 MHz, CDCl$_3$) δ; 7.55 (d, J=8.1 Hz, 4H), 7.60 (d, J=80 Hz, 4H), 7.35–7.09 (m, 12H), 6.32 (s, 1H), 4.01 (dd, J=9.3, 4.9 Hz, 2H), 3.53 (d, J=12.7 Hz, 2H), 3.19 (d, J=12.7 Hz, 2H), 2.79–2.71 (m, 2H), 2.45 (td, J=9.5, 6.3 Hz, 2H), 2.10–1.94 (m, 2H), 2.05 (s, 6H), 1.85–1.74 (m, 2H), 1.68–1.48 (m, 4H), $^{13}$C NMR (75 MHz, CDCl$_3$) δ; 156.1, 147.1, 146.7, 135.6, 128.1, 128.0, 126.6, 126.3, 125.9, 125.7, 122.6, 120.2, 78.7, 71.7, 54.3, 53.3, 29.7, 23.9, 19.7. MS(SIMS) 653.4 (M$^+$+1).

Example 13

Synthesis of Ligand 1n

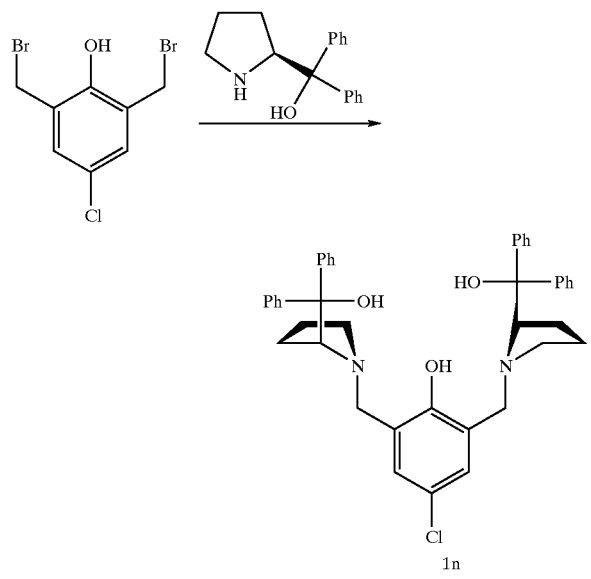

The dibromide 2,6-bis(bromomethyl)-4-chlorophenol (0.23 g, 0.747 mmol) was added in one portion to a stirred and cooled (0° C.) solution of (S)-diphenylprolinol (0.397 g, 1.56 mmol) and K$_2$CO$_3$ (0.86 g, 6.24 mmol) in dry DMF (3 mL). After the addition, the solution was brought to room temperature and stirring was continued for 12 h. The mixture was partitioned with Et$_2$O (20 mL) and H$_2$O (10 mL). The aqueous phase was extracted with Et$_2$O (10 mL×2), and the combined organic phases were washed with water and brine, dried (MgSO$_4$), and concentrated. The residue was purified over silica gel using 5 to 105 EtOAc-pet ether to give 1n (0.352 g, 72%) as a powder: [a]$^{25}$$_D$+69.64 (c 1.82, CH$_2$Cl$_2$); FTIR (CH$_2$Cl$_2$ cast) 3418, 3028, 2965, 1599 cm$^{-1}$; $^1$H NMR (300 MHz, CDCl$_3$) δ 1.46–1.70 (m, 4H), 1.72–1.88 (m, 2H), 1.94–2.08 (m, 2H), 2.36 (dd, J=16.2, 9.3 Hz, 2H), 2.78–2.88 (m, 2H), 3.20 (d, J=13.2 Hz, 2H), 3.36 (d, J=13.2 Hz, 2H), 3.96 (dd, J=8.8, 4.4 Hz, 2H), 6.75 (s, 2H), 7.10–7.36 (m, 12H), 7.56 (d, J=7.3 Hz, 4H), 7.66 (d, J=7.3 Hz, 4H); $^{13}$C NMR (75.5 MHz, CDCl$_3$) δ 24.06, 29.55, 5.11, 57.26, 71.31, 78.91, 122.61, 125.81, 125.89, 125.92, 126.49, 126.65, 127.54, 128.04, 128.20, 146.29, 146.75, 153.65.

Example 14

Enantioselective Aldol Reactions of Aryl Methyl Ketones (Table 1): Standard Procedure A. Preparation of Catalyst (Ligand:Zinc 1:2).

Under an argon atmosphere, a solution of diethylzinc (1M in hexane, 0.2 mL, 0.2 mmol) was added to a solution of 1a (64 mg, 0.1 mmol) in THF (1 mL) at ambient temperature, and the solution was stirred at the same temperature for 30 min.

B. Aldol Reaction.

Under an argon atmosphere, 0.25 mL of the catalyst solution prepared above (ca. 0.021 mmol) was added to a suspension of powdered 4A molecular sieves (100 mg, dried at 150° C. under vacuum overnight), aldehyde (0.5 mmol), acetophenone (600 mg, 0.6 mL, 5 mmol), and triphenylphosphine sulfide (22.1 mg, 0.075 mmol) in THF (0.8 mL) at 5° C. The mixture was stirred at the same temperature for 15 h–2 d. The reaction mixture was poured onto 1N HCl to remove the ligand, and the mixture was extracted with ether. The organic layer was washed with brine and dried over magnesium sulfate. Evaporation of the solvent under reduced pressure and purification of the residue by silica gel column chromatography afforded the product.

Characterizating Data for Products in Table 1

Entry 1

Previously reported in Narasaka et al., Chem. Lett. 1399 (1984).

$[\alpha]_D^{25}$+31.9 (c 0.75, CHCl$_3$). (56% ee).

Entry 2

(68% ee). $[\alpha]_D^{25}$+55.5 (c 4.07, CHCl$_3$). IR (neat) ν cm$^{-1}$; 3456, 2957, 1680, 1598, 1581, 1450, 1367, 1211, 1072, 1041. $^1$H NMR (300 MHz, CDCl$_3$) δ; 7.95 (d, J=7.3 Hz, 2H), 7.58 (t, J=7.3 Hz, 1H), 7.46 (t, J=7.3 Hz, 2H), 4.36–4.26 (m, 1H), 3.24 (d, J=3.2 Hz, 1H), 3.15 (dd, J=17.6, 2.7 Hz, 1H), 3.03 (dd, J=17.6, 8.6 Hz, 1H), 1.94–1.80 (m, 1H), 1.59 (ddd, J=13.9, 9.0, 5.4 Hz, 1H), 1.25 (ddd, J=13.9, 8.8, 4.4 Hz, 1H), 0.95 (d, J=6.6 Hz, 6H). $^{13}$C NMR (75 MHz, CDCl$_3$) δ; 201.0, 136.8, 133.5, 128.6, 128.0, 65.8, 45.6, 45.5, 24.4, 23.3, 22.0. Anal. Calcd for C$_{13}$H$_{18}$O$_2$: C, 75.69; H, 8.79. Found: C, 75.48; H, 8.60.

Entry 3

Previously reported in Veeraraghavan Ramachandran et al., Tet. Lett. 37:4911 (1996).

$[\alpha]_D^{25}$+77.6 (c 1.43, CHCl$_3$). (97% ee).

Entry 4

Previously reported in Narasaka et al., Chem. Lett. 1399 (1984).

$[\alpha]_D^{25}$+63.7 (c 1.54, CHCl$_3$). (98% ee)

Entry 5

(99% ee). mp 128° C. (from ether). $[\alpha]_D^{23}$+54.6 (c 1.17, CHCl$_3$). IR (KBr) νcm$^{-1}$; 3528, 1659, 1596, 1494, 1448, 1405, 1328, 1214, 1090, 1002. $^1$H NMR (300 MHz, CDCl$_3$) δ; 7.89–7.19 (m, 15H), 5.13–5.04 (m, 1H), 4.09 (d, J=9.3 Hz, 1H), 3.16 (dd, J=17.3, 7.8 Hz, 1H), 3.12 (bs, 1H), 3.08 (dd, J=17.3, 3.4 Hz, 1H). $^{13}$C NMR (75 MHz, CDCl$_3$) δ; 200.4, 142.0, 141.4, 136.7, 133.4, 128.8, 128.7, 128.6, 128.5, 128.3, 128.1, 126.8, 126.7, 70.0., 57.7, 43.5. Anal. Calcd for C$_{22}$H$_{20}$O$_2$: C, 83.52; H, 6.37. Found: C, 83.42; H, 6.22.

Entry 6

Previously reported in Meyers and Walkup, Tetrahedron 41:5089 (1985).

Major isomer 94% ee, minor isomer 98% ee.

Entry 7

(93% ee). $[\alpha]_D^{25}$+40.6 (c 1.9, CHCl$_3$). IR (neat) ν cm$^{-1}$; 3498, 2956, 2929, 2857, 1679, 1598, 1581, 1472, 1448, 1252, 1095, 837. $^1$H NMR (300 MHz, CDCl$_3$) δ; 7.97 (d, J=8.1 Hz, 2H), 7.55 (t, J=8.1 Hz, 1H), 7.45 (t, J=8.1 Hz, 2H), 4.20 (ddd, J=8.6, 3.9, 3.2 Hz, 1H), 3.65 (d, J=3.2 Hz, 1H), 3.52 (s, 2H), 3.14 (dd, J=16.4, 8.6 Hz, 1H), 3.07 (dd, J=16.4, 3.9 Hz, 1H), 0.98 (s, 3H), 0.90 (s, 12H), 0.07 (s, 6H). $^{13}$C NMR (75 MHz, CDCl$_3$) δ; 200.7, 137.3, 133.1, 128.5, 128.2, 73.9, 71.6, 40.8, 38.6, 25.8, 21.7, 19.5, 18.2, −5.6, −5.7. Anal. Calcd for C$_{19}$H$_{32}$O$_3$Si: C, 67.81; H, 9.58. Found: C, 67.96; H, 9.38.

Entry 8

Previously reported in Loh et al., *Tetrahedron* 55:10789 (1999).

$[\alpha]_D^{25}$+72.2 (c 1.2, CHCl$_3$). (97% ee).

Entry 9

(97% ee). $[\alpha]_D^{25}$+63.4 (c 1.06, CHCl$_3$). IR (neat) ν cm$^{-1}$; 3494, 2961, 1667, 1598, 1579, 1486, 1467, 1438, 1297, 1245, 1025, 758. $^1$H NMR (300 MHz, CDCl$_3$) δ; 7.70 (dd, J=7.8, 1.7 Hz, 1H), 7.47 (dt, J=8.8, 1.7 Hz, 1H), 7.03–6.90 (m, 2H), 3.96–3.80 (m, 1H), 3.90 (s, 3H), 3.27 (dd, J=17.6, 2.2 Hz, 1H), 3.23 (s, 1H), 2.97 (dd, J=17.6, 9.8 Hz, 1H), 1.84–1.70 (m, 1H), 0.98 (d, J=7.8 Hz, 3H), 0.95 (d, J=7.8 Hz, 3H). $^{13}$C NMR (75 MHz, CDCl$_3$) δ; 203.6, 158.7, 133.9, 130.2, 128.0, 120.7, 111.6, 72.7, 55.5, 47.3, 33.1, 18.4, 17.9. Anal. Calcd for C$_{13}$H$_{18}$O$_3$: C, 70.25; H, 8.16. Found: C, 70.40; H, 7.96.

Entry 10

(98% ee). mp 49° C. (from ether). $[\alpha]_D^{25}$+49.7 (c 3.35, CHCl$_3$). IR (KBr) ν cm$^{-1}$; 3482, 2966, 1676, 1601, 1576, 1509, 1422, 1261, 1218, 1173, 1031. $^1$H NMR (300 MHz, CDCl$_3$) δ; 7.92 (d, J=9.0 Hz, 2H), 6.91 (d, J=9.0 Hz, 2H), 3.99–3.91 (m, 1H), 3.85 (s, 3H), 3.37 (d, J=3.2 Hz, 1H), 3.11 (dd, J=17.3, 2.4 Hz, 1H), 2.94 (dd, J=17.3, 9.5 Hz, 1H), 1.83–1.72 (m, 1H), 0.99 (d, J=6.8 Hz, 3H),0.95 (d, J=6.8 Hz, 3H). $^{13}$C NMR (75 MHz, CDCl$_3$) δ; 199.8, 163.7, 130.3, 129.9, 113.7, 72.4, 55.4, 41.3, 33.1, 185, 17.8.

Anal. Calcd for C$_{13}$H$_{18}$O$_3$: C, 70.25; H, 8.16. Found: C, 70.40; H, 7.95.

Entry 11

(96% ee). mp 61–64° C. (from ether). $[\alpha]_D^{25}$+53.7 (c 1.33, CHCl$_3$). IR (KBr) ν cm$^{-1}$; 3518, 2949, 1665, 1626, 1470, 1373, 1213, 1184, 1122, 1008. $^1$H NMR (300 MHz, CDCl$_3$) δ; 8.45 (s, 1H), 8.01 (dd, J=8.5, 1.7 Hz, 1H), 7.96 (d, J=7.8 Hz, 1H), 7.90–7.84 (m, 2H), 7.63–7.52 (m, 2H), 4.10–4.02 (m, 1H), 3.32 (d, J=3.4 Hz, 1H), 3.29 (dd, J=17.3, 2.4 Hz, 1H), 3.16 (dd, J=17.3, 9.3 Hz, 1H), 1.91–1.79 (m, 1H), 1.06 (d, J=6.3 Hz, 3H), 1.03 (d, J=6.3 Hz, 3H). $^3$C NMR (75 MHz, CDCl$_3$) δ; 201.2, 135.7, 134.2, 132.4, 129.9, 129.6, 128.6, 128.5, 127.7, 126.8, 123.5, 72.4, 42.0, 33.1, 18.6, 17.9. Anal. Calcd for C$_{16}$H$_{18}$O$_2$: C, 79.31; H, 7.49. Found: C, 79.57; H, 7.23.

Example 15

Enantioselective Aldol Reactions of Acetone (Table 2): Standard Procedure

Catalyst generation: Under an argon atmosphere, a solution of diethylzinc (1M in hexanes, 0.4 ml, 0.4 mmol) was added to the solution of ligand 1 a (128 mg, 0.2 mmol) or 1m (130 mg, 0.2 mmol) in THF (2 ml) at r.t. After stirring for 30 min, with the evolution of ethane gas, the resulting solution (ca 0.1 M) was used as catalyst for the aldol reaction.

Aldol reaction: To a suspension of aldehyde (0.5 mmol), powdered molecular sieves (100 mg, dried at ca. 150° C. under vacuum overnight) and acetone (0.5 ml, 6.8 mmol) in THF (0.8 ml) was added the solution of catalyst (0.025 mmol for 5% catalyst, 0.05 mmol for 10% catalyst) at 0° C., and the mixture was stirred at 5° C. for 2 d. The resulting mixture was poured onto 1N HCl and extracted with ether. After normal workup, the crude product was purified by silica gel chromatography using a mixture of petroleum ether and ethyl acetate as eluent.

Characterizating Data for Products in Table 2.

Entry 1: (S)-4-Cyclohexyl-4-hydroxybutan-2-one

Previously reported in Silverman et al., *J. Org. Chem.* 52:180, 1987.

$[\alpha]_D^{25}$+50.1 (c 1.5, CHCl$_3$) ee=87% (lit. $[\alpha]_D^{25}$+52 (c 1.1, CCl$_4$)).

IR (neat) ν cm$^{-1}$; 3456, 2925, 2853, 2361, 1712, 1450, 1418, 1360, 1165. $^1$H NMR (300 MHz, CDCl$_3$) δ; 3.80 (bs, 1H), 2.90 (s, 1H), 2.63 (dd, J 17.3, 27 Hz, 1H), 2.53 (dd, J=17.3, 9.0 Hz, 1H), 2.18 (s, 3H), 1.86–0.92 (m, 11H). $^{13}$C NMR (75 MHz, CDCl$_3$) δ; 210.5, 71.6, 47.1, 42.9, 30.9, 28.8, 28.2, 26.4, 26.1, 26.0.

Entry 2: (S)-4-hydroxy-5-methylhexan-2-one

Previously reported in List, B. et al., *J. Am. Chem. Soc.* 122, 2395 (2000); Barbas, C. F.(III) et al., *J. Am. Chem. Soc.* 112, 2013 (1990).

$[\alpha]_D^{25}$+53.7 (c 1.5, CHCl$_3$) ee=91% (lit. $[\alpha]_D^{25}$+61.7 (c 0.6, CHCl$_3$)). $^1$H NMR (300 MHz, CDCl$_3$) δ; 3.84–3.75 (m, 1H), 2.95 (bs, 1H), 2.61 (dd, J=17.6, 3.0 Hz, 1H), 2.51 (dd, J=17.6, 9.0 Hz, 1H), 2.18 (s, 3H), 1.72–1.61 (m, 1H), 0.92 (d, J=7.4 Hz, 3H), 0.89 (d, J=7.1 Hz, 1H). $^{13}$C NMR (75 MHz, CDCl$_3$) δ; 210.4, 72.1, 46.9, 33.0, 30.8, 18.3, 17.7.

Entry 3: (S)-5,5-dimethyl-4-hydroxyhexan-2-one

Previously reported in Narasaka, K. et al., *Chem. Lett.* 1399 (1984).

$[\alpha]_D^{25}$+49.0 (c 0.8, CHCl$_3$) ee=86% (lit. $[\alpha]_D^{25}$+43.9 (c 0.8, CHCl$_3$) ee=86%, lit. $[\alpha]_D^{25}$+82.2 (c 0.6, CHCl$_3$) ee=83%).

Entry 4: 5,5-diphenyl-4-hydroxypentan-2-one ee=87%. $[\alpha]_D^{21.5}$+11.43 (c 0.9, CHCl$_3$). IR (neat) ν cm$^{-1}$; 3520 (OH), 1704 (C=O). $^1$H-NMR (300 MHz, CDCl$_3$) δ; 7.41–7.19 (m, 10H), 4.86 (m, 1H), 3.92 (d, J=9.0 Hz, 1H), 3.66 (m, 1H), 2.50 (m, 2H), 2.02 (s, 3H). $^{13}$C-NMR (75 MHz, CDCl$_3$) δ; 209.3, 141.9 141.2, 128.8, 128.7, 128.3, 127.2, 127.0, 126.8, 69.8, 57.6, 48.4, 30.9. MS (SIMS) M$^+$=254.3 Anal. calcd for C$_{17}$H$_{18}$O$_2$: C, 80.28; H, 7.13. Found C, 80.12; H, 7.14.

Entry 5: 4-hydroxy-6-methylheptan-2-one ee=84%. $[\alpha]_D^{21.5}$+47.04 (c 0.7, CHCl$_3$). IR (neat) ν cm$^{-1}$; 3410 (OH), 1712 (C=O). $^1$H-NMR (300 MHz, C$_6$D$_6$) δ; 3.75 (m, 1H), 2.22 (m, 2H), 2.17 (s, 3H), 2.11 (M, 1H), 1.21 (m, 2H), 0.99 (d, J=6.3 Hz, 6H). $^3$C-NMR (75 MHz, C$_6$D$_6$) δ; 195.9, 71.7, 48.5, 38.2, 30.4, 20.7, 17.5. MS (SIMS) M$^+$=144.2. Anal. calcd for C$_8$H$_{16}$O$_2$: C, 66.63; H, 11.18. Found C, 66.33; H, 11.08.

Entry 6: (S)-4-hydroxy-6-phenylhexan-2-one

Previously reported in Carreira, E. M. et al., *J. Am. Chem. Soc.* 117, 3649 (1995).

$[\alpha]_D^{25}$+19.9 (c 0.7, CHCl$_3$) ee=84% (lit. $[\alpha]_D^{25}$+20.6 (c 1.0, CHCl$_3$)).

Entry 7: (S)-4-hydroxyheptan-2-one

Previously reported in Paterson et al., *Tetrahedron Lett.* 30:997 (1989).

$[\alpha]_D^{25+42.3}$ (c 5.0, CHCl$_3$) ee=84% (lit. $[\alpha]_D^{25}$+35.1 (c 2.1, CHCl$_3$) ee=58%).

Entry 8: (S)-4-hydroxy-4-phenylbutan-2-one

Previously reported in Paterson et al., *Tetrahedron* 46, 4663 (1990).

$[\alpha]_D^{25}$+40.8 (c 1.0, CHCl$_3$) ee=79% (lit. $[\alpha]_D^{20}$+40.9 (c 10.3, CHCl$_3$) ee=78%).

Entry 9: 4-hydroxy-4-(4-nitrophenyl)butan-2-one

Previously reported in Grayson, D. H. et al., *J. Chem. Soc.*, Perkin I 2137 (1986).

Mp 62° C. (lit. 60–62° C.). ee=79%. $[\alpha]_D^{20}$+36.8 (c 1.7, CHCl$_3$). IR (neat) v cm$^{-1}$; 3493 (OH), 1710 (C=O). $^1$H-NMR (300 MHz, CDCl$_3$) δ; 8.20 (d, J=8.5 Hz, 2H), 7.52 (d, J=8.5 Hz, 2H), 5.20 (dd, J=7.3, 4.7 Hz, 1H), 4.77 (bs, 1H), 2.80 (m, 2H), 2.16 (s, 3H).
$^{13}$C-NMR (75 MHz, CDCl$_3$) δ; 208.6, 149.85, 140.2, 128.8, 124.2, 68.9, 51.5, 30.8. MS (SIMS) M$^+$=209.2. Anal. calcd for C$_{10}$H$_{11}$NO$_4$: C, 57.41; H, 5.30, N, 6.70. Found C, 57.29; H, 5.34; N, 6.72.

Example 16

Enantioselective Aldol Reactions of Methyl Vinyl Ketone (Table 3): Standard Procedure The procedure essentially as described for Table 2 (Example 15) was followed for the reaction of cyclohexanecarboxaldehyde (56 mg, 61 μL, 0.5 mmol) and MVK (1.5 mL), at a temperature of 0° C., replacing the additive Ph$_3$PS with those shown in Table 3. For preparation of catalyst, equimolar amounts of ligand and metal complex were used.

The product of entry 6 was purified by silica gel column chromatography (pet:ether, 1:1) to give 5-hydroxy-5-cyclohexyl penten-3-one, 58 mg, 0.324 mmol, 65%, 94% ee. t$_r$=23.76 min and 24.23 min (major enantiomer), (Chiral GC, CycloSil-B, 150° C.). IR (neat) v cm$^{-1}$; 3462, 2925, 2853, 1682, 1614, 1450, 1403, 1189, 989. $^1$H NMR (300 MHz, CDCl$_3$) δ; 6.36 (dd, J=17.6, 10.0 Hz, 1H), 6.25 (dd, J=17.6, 1.5 Hz, 1H), 5.89 (dd, J=10.0, 1.5 Hz, 1H), 3.90–3.82 (m, 1H), 2.97 (d, J=3.7 Hz, 1H), 2.80 (dd, J=17.3, 2.7 Hz, 1H), 2.69 (dd, J=17.3, 9.3 Hz, 1H), 1.90–1.00 (m, 11H). $^{13}$C NMR (75 MHz, CDCl$_3$) δ; 201.9, 136.8, 129.0, 71.6, 43.0, 42.9, 28.9, 28.3, 26.4, 26.2, 26.1.

Example 17

Enantioselective Aldol Reactions of Acetone and MVK Using Various Ligands (Table 4): Standard Procedure Under an argon atmosphere, a solution of diethylzinc (0.1 mmol) was added to a solution of indicated ligand (0.1 mmol) in toluene (1 mL) at ambient temperature; the solution was stirred for 30 minutes. This solution (0.5 mL) was added under argon to a solution of cyclohexanecarboxaldehyde (56 mg, 62 μL, 0.5 mmol), acetone or MVK (0.5 to 1.5 mL), and the indicated additive(s), at the indicated temperature, and the mixture was stirred at same temperature for 15 h–4 days, as indicated. The reaction mixture was poured onto 1N HCl, and the mixture was extracted with ether. The organic layer was washed with brine and dried over magnesium sulfate. Solvent was removed under reduced pressure and the residue purified by silica gel column chromatography (pet:ether, 1:1)

Example 18

Enantioselective Aldol Reactions of α-Hydroxyacetophenone (Table 6): Standard Procedure Under an argon atmosphere, a solution of diethylzinc (1M in hexane, 0.2 mL, 0.2 mmol) was added to a solution of 1a (64 mg, 0.1 mmol) in THF (1 mL) at ambient temperature, and the solution was stirred at the same temperature for 30 min.

This solution (0.25 mL) was added to a suspension of powdered 4A molecular sieves (100 mg, dried at 150° C. under vacuum overnight), aldehyde (0.5 mmol), and hydroxymethyl aryl ketone (0.75 mmol) in THF (1.5 mL) at −35° C. The mixture was stirred at the same temperature for 1–2 d. The reaction mixture was poured onto 1N HCl and extracted with ether. The organic layer was washed with brine and dried over magnesium sulfate. The solvent was removed under reduced pressure and the residue purified by silica gel column chromatography.

Characterizating Data for Products in Table 6

All compounds were purified by silica gel column chromatography, eluting with PE:AcOEt or PE:ether.

Entry 1.
Major diastereomer (less polar isomer):
t$_r$=7.44 min (major enantiomer) and 10.43 min, (Chiralcel OD, λ=254 nm, heptane:isopropanol=90:10, 1 mL/min). mp 77° C. $[\alpha]_D^{25}$-2.76 (c 3.0, CHCl$_3$, 91% ee).
IR (KBr) v cm$^{-1}$; 3457, 3060, 2920, 2850, 1682, 1599, 1578, 1449, 1395, 1257, 1119, 1037. $^1$H NMR (300 MHz, CDCl$_3$) δ; 7.86 (d, J=7.1 Hz, 2H), 7.62 (t, J=7.3 Hz, 1H), 7.50 (t, J=7.1 Hz, 2H), 5.22 (dd, J=5.1, 1.2 Hz, 1H), 3.99 (d, J=5.1 Hz, 1H), 3.58 (td, J=9.0, 1.2 Hz, 1H), 2.08–0.88 (m, 11H), 1.88 (d, J=10.3 Hz, 1H). $^{13}$C NMR (75 MHz, CDCl$_3$) δ; 200.8, 133.9, 133.6, 128.9, 128.4, 77.0, 73.2, 41.3, 29.4, 29.3, 26.3, 25.9, 25.8.
Anal. Calcd for C$_{15}$H$_{20}$O$_3$: C, 72.55; H, 8.12. Found: C, 72.74; H, 8.05.
Minor diastereomer (more polar isomer):
t$_r$=8.54 min and 9.77 min, (Chiralcel OD, λ=254 nm, heptane:isopropanol=90:10, 1 mL/min).

Entry 2.
Major diastereomer (less polar isomer):
t$_r$=6.15 min (major enantiomer) and 7.81 min, (Chiralcel OD, λ=254 nm, heptane:isopropanol=80:20, 1 mL/min). mp 86° C. $[\alpha]_D^{24}$-40.2 (c 1.32, CHCl$_3$, 86% ee). IR (KBr) v cm$^{-1}$; 3445, 2962, 2876, 1688, 1597, 1578, 1472, 1449, 1410, 1310, 1265, 1138. $^1$H NMR (300 MHz, CDCl$_3$) δ; 7.86 (d, J=7.3 Hz, 2H), 7.61 (t, J=7.3 Hz, 1H), 7.49 (t, J=7.8 Hz, 2H), 5.20 (d, J=3.4 Hz, 1H), 4.01 (d, J=4.6 Hz, 1H), 3.51 (t, J=9.3 Hz, 1H), 2.06 (d, J=10.5 Hz, 1H), 2.03–1.91 (m, 1H), 1.11 (d, J=6.6 Hz, 3H), 1.02 (d, J=6.8 Hz, 3H). $^{13}$C NMR (75 MHz, CDCl$_3$) δ; 200.7, 133.9, 133.6, 128.9, 128.4, 78.0, 73.6, 32.1, 19.2, 19.1. Anal. Calcd for C$_{12}$H$_{16}$O$_3$: C, 69.21; H, 7.74. Found: C, 69.36; H, 7.59.
Minor diastereomer (more polar isomer):
t$_r$=6.84 min (major enantiomer) and 7.25 min, (Chiralcel OD, λ=254 nm, heptane:isopropanol=80:20, 1 mL/min).

Entry 3.
Major diastereomer (less polar isomer):
t$_r$=12.50 min (major enantiomer) and 22.12 min, (Chiralcel AD, λ=254 nm, heptane:isopropanol=80:20, 1 mL/min). mp 161–166° C. $[\alpha]_D^{24}$-41.1 (c 1.02, CHCl$_3$, 81% ee). IR (KBr) v cm$^{-1}$; 3552, 3492, 3057, 3030, 2921, 1681, 1597, 1579, 1451, 1271, 1090, 979. $^1$H NMR (300 MHz, CDCl$_3$) δ; 7.67–7.14 (m, 15H), 4.91 (bd, J=2.7 Hz, 1H), 4.71 (dd, J=10.5, 8.1 Hz, 1H), 4.44 (d, J=10.5 Hz, 1H), 4.09 (bd, J=4.1 Hz, 1H), 2.17 (d, J=8.1 Hz, 1H), 1.02 (d, J=6.8 Hz, 3H). $^{13}$C NMR (75 MHz, CDCl$_3$) δ; 200.0, 141.5, 140.7, 133.9, 133.5, 129.0, 128.8, 128.6, 128.5, 128.44, 128.40, 127.2, 126.7, 74.5, 72.9, 55.3. Anal. Calcd for C22H$_{20}$O$_3$: C, 79.50; H, 6.06. Found: C, 79.66; H, 5.97.
Minor diastereomer (more polar isomer):
t$_r$=11.33 min (major enantiomer) and 14.08 min, (Chiralcel AD, λ=254 nm, heptane:isopropanol=80:20, 1 mL/min).

Entry 4a.
Major diastereomer (less polar isomer):
t$_r$=7.69 min (major enantiomer) and 9.48 min, (Chiralcel OD, λ=254 nm, heptane:isopropanol=90:10, 1 mL/min). mp 60–61° C. $[\alpha]_D^{25}$ −15.9 (c 1.58, CHCl$_3$, 88% ee). IR (KBr) ν cm$^{-1}$; 3333, 2951, 2867, 1684, 1598, 1580, 1470, 1450, 1319, 1249, 1148, 1104. $^1$H NMR (300 MHz, CDCl$_3$) δ; 7.88 (d, J=7.3 Hz, 2H), 7.62 (t, J=7.3 Hz, 1H), 7.50 (t, J=7.3 Hz, 2H), 4.95 (bs, 1H), 4.01 (bs, 2H), 2.01 (bs, 1H), 1.88–1.74 (m, 1H), 1.67 (ddd, J=13.7, 8.8, 6.1 Hz, 1H), 1.49 (ddd, J=13.7, 7.8, 4.9 Hz, 1H), 0.96 (d, J=6.6 Hz, 3H), 0.91 (d, J=6.6 Hz, 3H). $^{13}$C NMR (75 MHz, CDCl$_3$) δ; 200.3, 133.9, 133.8, 128.9, 128.4, 75.9, 71.0, 43.6, 24.5, 23.2, 22.1. Anal. Calcd for C$_{13}$H$_{18}$O$_3$: C, 70.25; H, 8.16. Found: C, 70.45; H, 7.95.

Minor diastereomer (more polar isomer):

$t_r$=14.02 min (major enantiomer) and 14.90 min, (Chiralcel OD, λ=254 nm, heptane:isopropanol=95:15, 1 mL/min). $^1$H NMR (300 MHz, CDCl$_3$) δ; 7.94 (d, J=7.3 Hz, 2H), 7.64 (t, J=7.3 Hz, 1H), 7.51 (t, J=7.3 Hz, 2H), 5.24 (bs, 1H), 4.02 (bd, J=10.3 Hz, 1H), 3.85 (bd, J=6.1 Hz, 1H), 2.24 (bs, 1H), 1.78–1.64 (m, 1H), 1.40 (ddd, J=14.2, 10.7, 4.9 Hz, 1H), 0.81 (d, J=6.8 Hz, 3H), 0.75 (ddd, J=14.2, 9.8, 2.7 Hz, 1H), 0.63 (d, J=6.6 Hz, 3H). $^{13}$C NMR (75 MHz, CDCl$_3$) δ; 199.8, 134.4, 134.1, 129.0, 128.6, 77.3, 71.5, 39.7, 24.1, 23.6, 21.1.

Entry 5a.

Major diastereomer (less polar isomer):

$t_r$=12.81 min and 14.26 (major enantiomer) min, % ee (Chiralcel OJ, λ=254 nm, heptane:isopropanol=80:20, 1 mL/min). mp 98° C. $[\alpha]_D^{26}$ +23.2 (c 1.42, CHCl$_3$, 90% ee). IR (KBr) ν cm$^{-1}$; 3463, 3024, 2952, 2856, 1692, 1598, 1578, 1496, 1448, 1398, 1242, 1132. $^1$H NMR (300 MHz, CDCl$_3$) δ; 7.77 (d, J=7.1 Hz, 2H), 7.60 (t, J=7.6 Hz, 1H), 7.44 (t, J=7.8 Hz, 2H), 7.34–7.18 (m, 5H), 4.99 (dd, J=5.6, 1.7 Hz, 1H), 4.01–3.92 (m, 1H), 3.95 (d, J=5.4 Hz, 1H), 2.92–2.74 (m, 2H), 2.18–1.98 (m, 2H), 1.87 (d, J=9.8 Hz, 1H). $^{13}$C NMR (75 MHz, CDCl$_3$) δ; 200.0, 141.2, 134.0, 133.5, 128.8, 128.5, 128.48, 128.40, 126.0, 75.3, 72.1, 35.9, 31.9. Anal. Calcd for C$_{17}$H$_{18}$O$_3$: C, 75.53; H, 6.71. Found: C, 75.62; H, 6.84.

Minor diastereomer (more polar isomer):

$t_r$=10.95 min and 11.91 (major enantiomer) min, (Chiralcel OJ, λ=254 nm, heptane:isopropanol=80:20, 1 mL/min). $^1$H NMR (300 MHz, CDCl$_3$) δ; 7.90 (d, J=7.1 Hz, 2H), 7.63 (t, J=7.6 Hz, 1H), 7.48 (t, J=7.8 Hz, 2H), 7.18–6.98 (m, 5H), 5.22 (dd, J=6.6, 3.7 Hz, 1H), 3.98–3.88 (m, 1H), 3.83 (d, J=6.6 Hz, 1H), 2.78 (ddd, J=13.9, 9.3, 4.9 Hz, 1H), 2.52 (ddd, J=13.9, 8.8, 7.8 Hz, 1H), 2.25 (bd, J=9.8 Hz, 1H), 1.78–1.65 (m, 1H), 1.45–1.34 (m, 1H). $^3$C NMR (75 MHz, CDCl$_3$) δ; 199.6, 141.2, 134.4, 133.9, 129.0, 128.6, 128.3, 128.2, 125.8, 76.9, 72.5, 32.4, 31.5.

Entry 7.

Major diastereomer (less polar isomer):

$t_r$=7.73 min (major enantiomer) and 9.33 min, (Chiralcel OD, λ=254 nm, heptane:isopropanol=90:10, 1 mL/min). mp 58–59° C. $[\alpha]_D^{25}$ −1.6 (c 1.67, CHCl$_3$, 86% ee). IR (KBr) ν cm$^{-1}$; 3414, 2920, 2851, 1683, 1596, 1578, 1452, 1424, 1316, 1279, 1254, 1101. $^1$H NMR (300 MHz, CDCl$_3$) δ; 7.88 (d, J=7.3 Hz, 2H), 7.62 (t, J=7.3 Hz, 1H), 7.50 (t, J=7.3 Hz, 2H), 5.00 (dd, J=5.6, 1.5 Hz, 1H), 3.97 (d, J=5.6 Hz, 1H), 3.96–3.87 (m, 1H), 1.96 (d, J=9.5 Hz, 1H), 1.78–1.66 (m, 2H), 1.54–1.22 (m, 10H), 0.88 (t, J=6.8 Hz, 13H). $^{13}$C NMR (75 MHz, CDCl$_3$) δ; 200.3, 134.0, 133.8, 128.9, 128.5, 75.5, 72.9, 34.7, 31.8, 29.5, 29.2, 25.9, 22.6, 14.1. Anal. Calcd for C$_{16}$H$_{24}$O$_3$: C, 72.69; H, 9.15. Found: C, 72.70; H, 9.22.

Minor diastereomer (more polar isomer):

$t_r$=13.38 min (major enantiomer) and 14.73 min, (Chiralcel OD, λ=254 nm, heptane:isopropanol=95:5, 1 mL/min). $^1$H NMR (300 MHz, CDCl$_3$) δ; 7.95 (d, J=73 Hz, 2H), 7.64 (t, J=7.3 Hz, 1H), 7.51 (t, J=7.3 Hz, 2H), 5.23 (dd, J=6.6, 3.7 Hz, 1H), 3.98–3.88 (m, 1H), 3.96–3.87 (m, 1H), 3.84 (d, J=6.6 Hz, 1H), 2.26 (d, J=9.8 Hz, 1H), 1.44–1.00 (m, 12H), 0.82 (t, J=6.8 Hz, 3H). $^{13}$C NMR (75 MHz, CDCl$_3$) δ; 199.8, 134.3, 134.1, 129.0, 128.6, 77.0, 73.3, 31.7, 30.8, 29.2, 29.0, 25.4, 22.6, 14.0.

Entry 8.

Major diastereomer (less polar isomer):

$t_r$=7.64 min (major enantiomer) and 9.26 min, (Chiralcel OD, λ=254 nm, heptane:isopropanol=90:10, 1 mL/min). mp 62° C. $[\alpha]_D^{25}$ +0.64 (c 2.46, CHCl$_3$, 87% ee). IR (KBr) ν cm$^{-1}$; 3462, 3374, 2917, 2849, 1690, 1642, 1598, 1582, 1450, 1270, 1116. $^1$H NMR (300 MHz, CDCl$_3$) δ; 7.88 (d, J=7.3 Hz, 2H), 7.62 (t, J=7.3 Hz, 1H), 7.50 (t, J=7.3 Hz, 2H), 5.81 (ddt, J=17.1, 10.3, 6.6 Hz, 1H), 5.03–4.90 (m, 3H), 3.96 (d, J=5.9 Hz, 1H), 3.95–3.87 (m, 1H), 2.04 (q, J=6.8 Hz, 2H), 1.94 (d, J=9.5 Hz, 1H), 1.70 (q, J=7.8 Hz, 2H), 1.55–1.20 (m, 12H). $^{13}$C NMR (75 MHz, CDCl$_3$) δ; 200.3, 139.1, 133.9, 133.8, 128.9, 128.5, 114.1, 75.4, 72.9, 34.7, 33.7, 29.5, 29.4, 29.3, 29.1, 28.9, 25.8. Anal. Calcd for C$_{19}$H$_{28}$O$_3$: C, 74.96; H, 9.27. Found: C, 75.11; H, 9.12.

Minor diastereomer (more polar isomer):

$t_r$=13.76 min (major enantiomer) and 14.97 min, (Chiralcel OD, λ=254 nm, heptane:isopropanol=95:5, 1 m/min). $^1$H NMR (300 MHz, CDCl$_3$) δ; 7.95 (d, J=7.3 Hz, 2H), 7.64 (t, J=7.3 Hz, 1H), 7.51 (t, J=7.3 Hz, 2H), 5.78 (ddt, J=17.1, 10.3, 6.6 Hz, 1H), 5.23 (dd, J=6.6, 3.7 Hz, 1H), 5.00–4.87 (m, 2H), 3.98–3.87 (m, 1H), 3.85 (d, J=6.6 Hz, 1H), 2.30 (d, J=9.8 Hz, 1H), 2.00 (q, J=6.9 Hz, 2H), 1.44–1.00 (m, 14H).

$^{13}$C NMR (75 MHz, CDCl$_3$) δ; 199.8, 139.2, 134.3, 134.1, 129.0, 128.6, 114.1, 77.0, 73.3, 33.7, 36.7, 29.3, 29.2, 29.0, 28.8, 25.4.

Entry 9.

Major diastereomer (less polar isomer):

$t_r$=13.38 min and 19.47 min, (Chiralcel AD, λ=254 nm, heptane:isopropanol=80:20, 1 mL/min). mp 89° C. $[\alpha]_D^{24}$ −6.8 (c 1.49, CHCl$_3$, 96% ee). IR (KBr) ν cm$^{-1}$; 3491, 3374, 3133, 2926, 1855, 1852, 1562, 1467, 1384, 1297, 1044. $^1$H NMR (300 MHz, CDCl$_3$); δ 7.61 (d, J=1.7 Hz, 1H), 7.32 (d, J=3.7 Hz, 1H), 6.58 (dd, J=3.7, 1.7 Hz, 1H), 4.96 (dd, J=5.6, 0.9 Hz, 1H), 3.83 (d, J=5.6 Hz, 1H), 3.73 (dt, J=8.8 Hz, 1H), 2.1–0.93 (m, 12H). $^{13}$C NMR (75 MHz, CDCl$_3$) δ; 189.1, 150.3, 146.9, 119.0, 112.6, 76.8, 73.7, 41.0, 29.4, 29.2, 26.3, 25.9, 25.8. Anal. Calcd for C$_{13}$H$_{18}$O$_4$: C, 65.53; H, 7.61. Found: C, 65.39H, 7.70.

Minor diastereomer (more polar isomer):

$t_r$=9.97 min and 11.46 min, (Chiralcel AD, λ=254 nm, heptane:isopropanol=80:20, 1 mL/min). $^1$H NMR (300 MHz, CDCl$_3$) δ; 7.66 (bs, 1H), 7.36 (d, J=3.7 Hz, 1H), 6.60 (dd, J=3.7, 1.7 Hz, 1H), 4.90 (dd, J=7.6, 5.4 Hz, 1H), 3.72–3.66 (m, 1H), 3.50 (d, J=7.8 Hz, 1H), 2.21 (d, J=83 Hz, 1H), 2.1–0.9 (m, 11H).

Entry 10.

Major diastereomer (less polar isomer):

$t_r$=13.84 min and 16.64 min, (Chiralcel AD, λ=254 nm, heptane:isopropanol=80:20, 1 mL/min). mp 100° C. $[\alpha]_D^{24}$ +25.8 (c 1.69, CHCl$_3$, 95% ee). IR (KBr) ν cm$^{-1}$; 3414, 3386, 3122, 2903, 1665, 1561, 1463, 1388, 1294, 1080, 1031. $^1$H NMR (300 MHz, CDCl$_3$) δ; 7.57 (d, J=1.7 Hz, 1H), 7.33–7.17 (m, 6H), 6.56 (dd, J=3.7, 1.7 Hz, 1H), 4.77 (dd, J=5.8, 1.7 Hz, 1H), 4.16–4.06 (m, 1H), 3.82 (d, J=5.8 Hz, 1H), 2.96–2.73 (m, 2H), 2.15–1.98 (m, 3H). $^{13}$C NMR (75 MHz, CDCl$_3$) δ; 188.2, 150.2, 147.1, 141.4, 128.4, 125.9, 119.3, 112.7, 75.8, 72.0, 35.9, 32.0. Anal. Calcd for $C_{15}H_{16}O_4$: C, 69.22; H, 6.20.

Found: C, 69.40; H, 6.23.

Minor diastereomer (more polar isomer):

$t_r$=10.46 min and 11.78 min, (Chiralcel AD, λ=254 nm, heptane:isopropanol=80:20, 1 mL/min). $^1$H NMR (300 MHz, CDCl$_3$) δ; 7.60 (d, J=1.7 Hz, 1H), 7.32 (d, J=3.7 Hz, 1H), 7.27–7.06 (m, 5H), 6.57 (dd, J=3.7, 1.7 Hz, 1H), 4.95 (dd, J=6.8, 3.9 Hz, 1H), 4.04 (tt, J=10.3, 3.2 Hz, 1H), 3.67 (d, J=6.8 Hz, 1H), 2.83 (ddd, J=13.9, 9.0, 5.1 Hz, 1H), 2.61 (ddd, J=13.9, 8.3, 8.0 Hz, 1H), 2.33 (d, J=9.8 Hz, 1H), 1.82–1.47 (m, 2H). $^{13}$C NMR (75 MHz, CDCl$_3$) δ; 187.7, 150.5, 147.6, 141.4, 128.3, 125.8, 119.7, 112.8, 77.0, 72.4, 32.8, 31.6.

Example 19

Preparation of Diol of Known Configuration for Determination of Absolute Stereochemistries

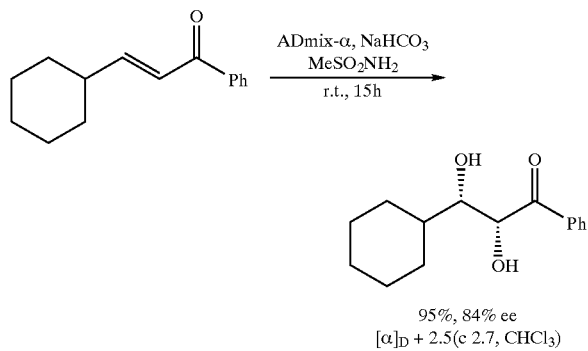

A solution of the α,β-unsaturated ketone (40 mg, 0.19 mmol) in t-butanol (0.5 mL) was added to the mixture of 300 mg of ADmix-α (reagent for Sharpless asymmetric dihydroxylation; see *J. Org. Chem.* 57:2768, 1992; available from ChiRex, Wellesley, Mass.), 50 mg of sodium bicarbonate, 20 mg of methanesulfonamide in 0.5 mL of t-butanol, and 0.5 mL of water. The mixture was stirred at ambient temperature for 15 h. NaHSO$_3$ was added to the mixture, and it was extracted with ether. The organic layer was washed with brine and dried over magnesium sulfate. Evaporation of the solvent under the reduced pressure and purification of the residue by silica gel column chromatography (PE:ether, 1:1) afforded the diol product (42 mg, 0.181 mmol, 95%, 84% ee). $[\alpha]_D^{25}$+2.5 (c 2.7, CHCl$_3$).

Example 20

Enantioselective Nitro-Aldol Reactions of Nitromethane (Tables 7–8): Representative Procedure A. Preparation of Catalyst Under an argon atmosphere, a solution of diethylzinc (0.36 mL, 1.1 M in tol, 0.4 mmol) was added to a stirred and cooled (0° C.) solution of ligand (0.128 g, 0.2 mmol) in THF (2 mL). After the addition the cold bath was removed and the solution was allowed to stir at room temperature for 30 min to make a 0.1M catalyst solution.

B. Nitro-Aldol Reaction

Under an argon atmosphere, a solution of catalyst (0.5 mL, 0.1 M in THF, 0.05 mmol) was added dropwise to a stirred and cooled (–78° C.) suspension of powdered molecular sieves 4A (100 mg, dried at 120° C. under vacuum overnight), aldehyde (1 mmol), and CH$_3$NO$_2$ (0.32 mL, 6 mmol) in THF (3 mL). After the addition, the resulting mixture was transferred to a –20° C. cold bath and left to stir for 24 h. The reaction was quenched by adding aqueous HCl solution (3 mL, 0.5 M), and the resulting mixture was partitioned with Et$_2$O (10 mL). The organic phase was washed with water and brine, dried (MgSO4), and filtered. After the evaporation of the solvent, the residue was purified by silica gel column chromatography (EtOAc:pet ether, 10:90) to afford the nitro aldol product.

Characterizating Data for Products in Tables 7–8

All products were purified on silica gel using a EtOAc/pet ether gradient.

Table 7, all entries.

$[\alpha]_D^{25}$+15.87 (c 5.01, CHCl$_3$) (85% ee); $^1$H NMR (300 MHz, CDCl$_3$) δ 1.0–1.61 (m, 5H), 1.72–1.52 (m, 1H), 1.55–1.85 (5H), 2.58 (br s, 1H), 4.02–4.12 (m, 1H), 4.35–4.50 (m, 2H); $^{13}$C NMR (75.5 MHz, CDCl$_3$) δ 25.69, 25.82, 26.02, 27.89, 28.75, 41.37, 42.81, 79.28.

See Sasai, H. et al., *J. Am. Chem. Soc.*, 1992, 114, 4419.

Table 8, Entry 1

$[\alpha]_D^{25}$+5.44 (c 2.49, CHCl$_3$) (88% ee); $^1$H NMR (300 MHz, CDCl$_3$) δ 0.97 (d, J=4.4 Hz, 3H), 1.02 (d, J=4.1 Hz, 3H), 1.80 (oct, J=6.8 Hz, 1H), 4.1 (ddd, J=5.8, 5.8, 3.2 Hz, 1H), 4.40 (dd, J=13.2, 8.55 Hz, 1H), 4.48 (dd, J=13.2, 3.2 Hz, 1H); $^{13}$C NMR (75.5 MHz, CDCl$_3$) δ 17.44, 18.43, 31.69, 73.31, 79.23.

Entry 2

$[\alpha]_D^{25}$+29.39 (c 3.39, CH$_2$Cl$_2$) (93% ee); $^1$H NMR (300 MHz, CDCl$_3$) δ 0.95 (s, 9H), 2.40 (br s, 1H), 4.04 (d, J=9.77 Hz, 1H), 4.37 (dd, J=12.9, 10.0 Hz, 1H), 4.52 (dd, J=12.9, 2.2 Hz, 1H); $^{13}$C NMR (75.5 MHz, CDCl$_3$) δ 25.58, 34.27, 76.14, 78.19.

Entry 3

$[\alpha]_D^{25}$+16.32 (c 2.10, CH$_2$Cl$_2$) (92% ee); FTIR (film) 3442, 1554, 1463, 1383 cm$^{-1}$; $^1$H NMR (300 MHz, CDCl$_3$) δ 0.94 (t, J=7.32, 6H), 1.20–1.56 (m, 5H), 2.38 (d, J=4.6 Hz, 1H), 4.32–4.42 (m, 1H), 4.43 (s, 1H), 4.46 (d, J=2.2 Hz, 1H); $^{13}$C NMR (75.5 MHz, CDCl$_3$) δ 6.60, 6.68, 16.51, 17.03, 39.91, 65.37, 74.65.

Entry 4

$[\alpha]_D^{25}$ –2.17 (c 1.95, CH$_2$Cl$_2$) (87% ee); FTIR (film) 3442, 2960, 1555, 1469, 1385 cm$^{-1}$;

$^1$H NMR (300 MHz, CDCl$_3$) δ 0.95 (d, J=4.4 Hz, 3H), 0.97 (d, J=4.4 Hz, 3H), 1.16–1.30 (m, 1H), 1.44–1.56 (m, 1H), 1.76–1.90 (m, 1H), 2.48 (d, J=2.7 Hz, 1H), 4.32–4.44 (m, 3H);); $^{13}$C NMR (75.5 MHz, CDCl$_3$) δ 21.73, 23.17, 24.29, 42.39, 66.92, 80.93.

Entries 5a–b $[\alpha]_D^{25}$–13.56 (c1.32, CH$_2$Cl$_2$) (85% ee); $^1$H NMR (300 MHz, CDCl$_3$) δ 1.72–1.94 (m, 2H), 2.64 (br s, 1H), 2.20–2.92 (m, 2H), 4.26–4.35 (m, 1H), 4.39 (d, J=1.9 Hz, 1H), 4.41 (s, 1H), 7.18–7.38 (m, 5H); $^{13}$C NMR (75.5 MHz, CDCl$_3$) δ 31.29, 35.06, 67.69, 80.49, 126.31, 128.40, 128.62, 140.55; mp 87° C.

Entry 6

$[\alpha]_D^{25}$+0.52 (c 0.59, CH$_2$Cl$_2$) (86% ee); FTIR (film) 3432, 2930, 1556 cm$^{-1}$; $^1$H NMR (300 MHz, CDCl$_3$) δ 1.85 (q, J=11.2, 6.1 Hz, 2H), 3.34 (d, J=3.7 Hz, 1H), 3.64–3.76 (m, 2H), 4.44 (dd, J=17.1, 6.8 Hz, 2H), 4.44–4.60 (m, 1H), 4.53 (s, 2H), 7.21–7.43 (m, 5H); $^{13}$C NMR (125.6 MHz, CDCl$_3$) δ 33.22, 67.26, 67.94, 73.46, 80.38, 127.74, 127.98, 128.56, 137.42. Anal. Calcd for $C_{11}H_{15}NO_4$: C. 58.66; H, 6.71.

Entry 7

$[\alpha]_D^{25}$–1.03 (c 1.70, CH$_2$Cl$_2$) (19:1 dr); FTIR (film) 3441, 2922, 1555, 1452, 1381 cm$^{-1}$; $^1$H NMR (500 MHz, CDCl$_3$)

δ 0.98 (d, J=6.6 Hz, 3H), 1.16–1.50 (m, 4H), 1.60 (ddd, J=10.2, 3.4, 3.4 Hz, 1H), 1.62 (s, 3H), 1.71 (s, 3H), 1.72–1.80 (m, 1H), 1.94–2.09 (m, 2H), 2.46 (dd, J=4.6, 1.46 Hz, 1H), 4.36–4.48 (m, 3H), 5.08–5.14 (m, 1H); $^{13}$C NMR (125.6 MHz, CDCl$_3$) δ 17.93, 19.13, 25.59, 25.96, 28.71, 37.79, 40.83, 66.85, 81.34, 124.50, 131.91. Anal. Calcd for C$_{11}$H$_{21}$NO$_3$: C. 61.37; H, 9.83.

Entry 8

[α]$^{25}_D$ +33.02 (c 3.71, CH$_2$Cl$_2$) (91% ee); $^1$H NMR (300 MHz, CDCl$_3$) δ 2.80 (br s, 1H), 4.52 (dd, J=13.4, 3.2 Hz, 1H), 4.62 (dd, J=13.4, 9.3, 1H), 5.48 (dd, J=7.31, 3.21H), 7.32–7.50 (m, 5H); $^{13}$C NMR (125.6 MHz, CDCl$_3$) δ 70.98, 81.19, 125.92, 128.98, 129.03, 138.26.

Entry 9

[α]$^{25}_D$ +17.67 (c 2.41, CH$_2$Cl$_2$) (93% ee), FTIR (film) 3541, 1552, 1418, 1378 cm$^{-1}$; $^1$H NMR (500 MHz, CDCl$_3$) δ 2.80 (br s, 1H), 4.62 (dd, J=14.2, 10.2 Hz, 2H), 6.22 (dd, J=9.0, 3.2 Hz, 1H), 7.44–7.56 (m, 3H), 7.72 (d, J=7.1 Hz, 1H), 7.80 (d, J=8.3 Hz, 1H), 7.84 (d, J=8.1 Hz, 1H), 7.99 (d, J=8.6 Hz, 1H); $^{13}$C NMR (125.6 MHz, CDCl$_3$) δ 68.30, 80.77, 121.79, 123.86, 125.51, 126.10, 127.09, 129.32, 129.43, 129.53, 133.50, 133.73.

Entry 10

[α]$^{25}_D$ +26.79 (c 2.02, CH$_2$Cl$_2$) (78% ee), FTIR (film) 3489, 2939, 2839, 1608, 1552, 1517, 1465, 1379 cm–1; $^1$H NMR (300 MHz, CDCl$_3$) δ 3.87 (s, 3H), 3.89 (s, 3H), 4.48 (dd, J=13.2, 3.2 Hz, 1H), 4.61 (dd, J=13.2, 9.5 Hz, 1H), 5.40 (dd, J=9.5, 2.9 Hz, 1H), 6.83–6.95 (m, 3H); $^{13}$C NMR (125.6 MHz, CDCl$_3$) δ 55.92, 55.93, 70.85, 81.29, 108.73, 111.22, 118.31, 130.59, 149.38.

Entry 11

[α]$^{25}_D$ 5.87 (c 1.26, CH$_2$Cl$_2$) (92% ee); FTIR (film): 3518, 2982, 1736, 1557, 1341, 1131 cm$^{-1}$; $^1$H NMR (CDCl$_3$, 300 MHz) δ 1.60 (s, 9H), 4.18 (d, J=7.1 Hz, 1H), 4.84–4.68 (m, 2H), 5.72–5.65 (m, 1H), 6.12 (t, J=3.4, 1H), 7.19 (dd, J=3.4, 1.7 Hz, 1H); $^{13}$C NMR (75 MHz, CDCl$_3$) δ 27.9, 64.9, 78.8, 85.5, 110.6, 113.1, 122.9, 131.8, 150.0 cm$^{-1}$.

Example 21

Preparation of Mandelic Acid Derivative for Determination of Absolute Configuration

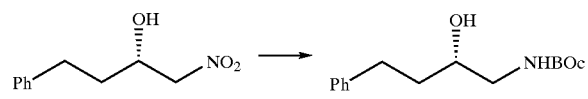

The nitroaldol adduct of nitromethane with 3-phenyl propionaldehyde (Table 8, entries 5a–b) (0.1 g, 0.51 mmol) was stirred in the presence of 10% Pd/C (20 mg) in MeOH (2.5 mL) under H$_2$ atmosphere (1 atm) for 3 h. The mixture was then filtered through a pad of celite, using MeOH as wash, and the solvent was evaporated. The crude amine was re-dissolved in CH$_2$Cl$_2$ (5 mL) and i-Pr$_2$NEt (0.18 mL, 1.02 mmol), and (BOC)$_2$O (0.123 g, 0.563 mmol) was subsequently introduced into the reaction solution. After the mixture was allowed to stir for 3 h at rt, it was diluted with EtOAc and washed with sat. NH$_4$Cl solution, water, and brine, dried (MgSO$_4$), and concentrated. The residue was purified over silica gel chromatography column using 10% EtOAc/pet ether to give a clear oil (0.104 g, 77%): [α]$^{25}_D$– 8.86 (c 0.56, CH$_2$Cl$_2$), FTIR (film) 3446, 2955, 1703, 1510, 1265 cm$^{-1}$; $^1$H NMR (500 MHz, CDCl$_3$) δ1.46 (s, 9H), 1.79 (q, J=7.5 Hz, 2H), 2.72 (ddd, J=13.9, 8.1, 8.1 Hz, 1H), 2.83 (ddd, J=13.4, 8.1, 8.1 Hz, 1H), 3.06–3.14 (m, 1H), 3.32 (br d, J=14.2 Hz, 1H), 3.70–3.77 (m, 1H), 4.95 (br s, 1H), 7.20–7.24 (m, 3H), 7.28–7.32 (m, 2H); $^{13}$C NMR (125.6 MHz, CDCl$_3$) δ 28.35, 31.80, 36.37, 46.70, 71.06, 79.71, 125.92, 128.39, 128.43, 141.71.

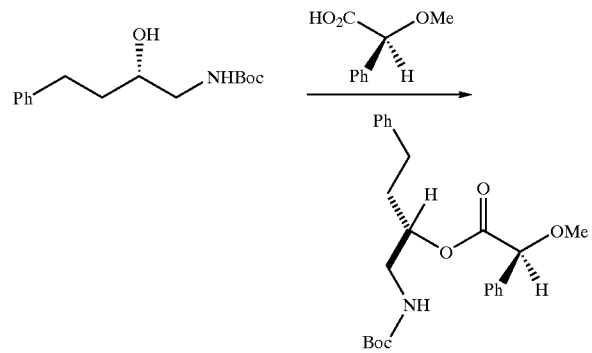

EDCI (1-ethyl-3-(3-dimethylaminopropyl)carbodiimide; 59 mg, 0.307 mmol) was added to a stirred solution of the protected amine, above (51 mg, 0.192 mmol), (S)-(+)-α-methoxy phenylacetic acid (48 mg, 0.288 mmol), and DMAP (2 mg, 0.019 mmol) in CH$_2$Cl$_2$ (3 mL). The solution was allowed to stir for 5 h at rt, and it was then diluted with Et$_2$O (20 mL) and washed with 0.5 N HCl, saturated NaHCO$_3$ solution, and brine. The organic phase was dried (MgSO4) and concentrated to give the methoxy ester product as a clear oil: [α]$^{25}_D$+41.72 (c 4.30, CH$_2$Cl$_2$); FTIR (film) 3435, 3061, 2979, 1749, 1713, 1606, 1508, 1266, 1171 cm–1; $^1$H NMR (500 MHz, CDCl$_3$) δ 1.41, 1.81–1.96 (m, 2H), 2.62 (t, J=8.1 Hz, 2H), 3.02 (ddd, J=14.2, 14.2, 6.9 Hz, 1H), 3.30 (ddd, J=17.8, 6.3, 3.4 Hz, 1H), 3.44 (s, 3H), 4.02 (br s, 1H), 5.03 (dddd, J=8.0, 7.5, 7.5, 4.9 Hz, 1H), 7.10–7.50 (m, 10H); $^{13}$C NMR (125.6 MHz, CDCl$_3$) δ 28.57, 31.68, 33.44, 43.76, 57.57, 74.24, 79.65, 82.70, 126.30, 127.32, 128.56, 128.70, 129.11, 129.24, 136.78, 141.28, 155.92, 170.59.

Example 22

Conversion of Nitroaldol Product into Chiral α-Hydroxy Carboxylic Ester

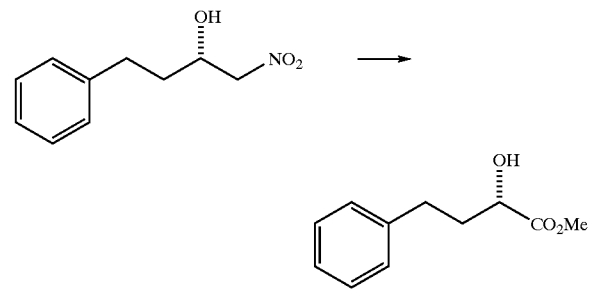

NaNO$_2$ (0.18 g, 2.61 mmol) was added in one portion to a stirred solution of the nitroaldol adduct of nitromethane with 3-phenyl propionaldehyde (Table 8, entries 5a–b) (0.17 g, 0.871 mmol, 84% ee) in AcOH (0.54 mL, 8.71 mmol) and DMSO (2 mL). The resulting solution was stirred overnight at rt and for 3 h at 35° C. The reaction was quenched with 0.5 HCl (5 mL) and extracted with CH$_2$Cl$_2$ (5 mL×4) and EtOAc (2 mL×2). The combined organic phases were dried (Na$_2$SO$_4$) and the residue was purified over silica gel using 50% EtOAc/pet ether to give the carboxylic acid. This product was redissolved in $Et_2O$ and treated with $TMSCHN_2$ to give the ester (0.11 g, 69%) as an oil: $[\alpha]^{25}_D$+29.5 (c 1.02, $CH_2Cl_2$) (85% ee), tr=10.88 (major) and 17.12 min (Chiralcel AD, λ=254 nm, heptane:isopropanol 95:5, 0.95 ml/min).

While the invention has been described with reference to specific methods and embodiments, it will be appreciated that various modifications may be made without departing from the invention.

What is claimed is:

1. A chiral ligand of formula I:

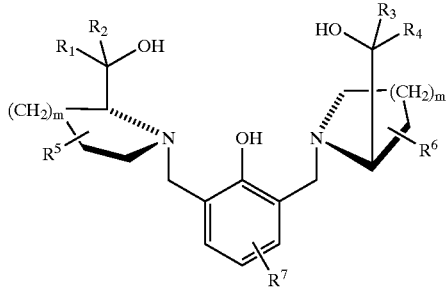

where
$R^1$–$R^4$ are aryl groups, which may be the same or different, each of which is unsubstituted or substituted with one or more substituents X, where each X is independently selected from alkyl, alkenyl, alkynyl, aryl, aralkyl, aralkenyl, aralkynyl, alkoxy, aryloxy, amide, alkyl- or aryl sulfonyl, sulfonamide, hydroxy, cyano, nitro, and halogen, wherein $R^1$ and $R^2$, or $R^3$ and $R^4$, or both of these combinations, may be linked at an α-carbon of each said group to form a tricyclic or larger ring system;

m is an integer from 0 to 3;

each of $R^5$ and $R^6$ represents one or more substituents independently selected from the group consisting of hydrogen and X as defined above; and $R^7$ represents one or more substituents on the phenol ring independently selected from the group consisting of hydrogen, X as defined above, and a further fused ring.

2. The ligand of claim 1, wherein each of $R^1$–$R^4$ is phenyl, α-naphthyl, or β-naphthyl, unsubstituted or substituted with a group selected from X as defined in claim 1.

3. The ligand of claim 2, wherein each of $R^1$–$R^4$ is phenyl, α-naphthyl, or β-naphthyl, unsubstituted or substituted with a group selected from lower alkyl, lower alkoxy, and halogen.

4. The ligand of claim 1, wherein m is 1.

5. The ligand of claim 4, wherein each of $R^5$ and $R^6$ is hydrogen.

6. The ligand of claim 1, wherein each $R^7$ is independently selected from hydrogen, lower alkyl, lower alkoxy, and halogen.

7. The ligand of claim 1, selected from the group consisting of ligands 1a–1n as disclosed herein.

8. The ligand of claim 7, selected from the group consisting of ligands 1a, 1c–d, and 1m as disclosed herein.

* * * * *